(12) United States Patent
Fantuzzi et al.

(10) Patent No.: US 12,369,944 B2
(45) Date of Patent: Jul. 29, 2025

(54) VARIABLE SIZE REPOSITIONING SHEATH

(71) Applicant: ABIOMED, Inc., Danvers, MA (US)

(72) Inventors: Glen Fantuzzi, Danvers, MA (US); Christopher Korkuch, Danvers, MA (US); Caitlyn Hastie, Danvers, MA (US); Robert Fishman, Danvers, MA (US); Akshay Ashok, Danvers, MA (US); John Modlish, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 18/418,468

(22) Filed: Jan. 22, 2024

(65) Prior Publication Data

US 2024/0307091 A1     Sep. 19, 2024

Related U.S. Application Data

(63) Continuation of application No. 16/854,357, filed on Apr. 21, 2020, now Pat. No. 11,911,072.

(Continued)

(51) Int. Cl.
*A61B 17/34* (2006.01)
*A61M 60/148* (2021.01)
(Continued)

(52) U.S. Cl.
CPC ...... *A61B 17/3439* (2013.01); *A61B 17/3468* (2013.01); *A61M 60/148* (2021.01);
(Continued)

(58) Field of Classification Search
CPC ............ A61B 17/3439; A61B 17/3415; A61B 17/3423; A61B 17/3431; A61B 17/3462;
(Continued)

(56) References Cited

U.S. PATENT DOCUMENTS 5,334,164 A     8/1994 Guy et al.
11,911,072 B2 * 2/2024 Fantuzzi ............. A61M 60/414
(Continued)

FOREIGN PATENT DOCUMENTS

CN     106659877 A     5/2017
EP     2962721 A1 *   1/2016   ........... A61B 5/0215
(Continued)

OTHER PUBLICATIONS

International Search Report and Written Opinion for Application No. PCT/US2020/029089 dated Sep. 1, 2020.
(Continued)

*Primary Examiner* — Jon Eric C Morales
(74) *Attorney, Agent, or Firm* — Botos Churchill IP Law LLP

(57) ABSTRACT

Systems and methods are provided for insertion of a medical device into a blood vessel. The system may include a sheath assembly with an introducer sheath and a variable size repositioning sheath. The variable size repositioning sheath may be configured to be adjustable in size in a radial direction and to be inserted into the blood vessel or an expandable introducer sheath. In some aspects, the system may include an intracardiac device such as a blood pump with an elongate catheter.

13 Claims, 5 Drawing Sheets

Related U.S. Application Data

(60) Provisional application No. 62/836,960, filed on Apr. 22, 2019.

(51) Int. Cl.
| | |
|---|---|
| *A61M 60/174* | (2021.01) |
| *A61M 60/216* | (2021.01) |
| *A61M 60/414* | (2021.01) |
| *A61M 60/416* | (2021.01) |
| *A61M 60/554* | (2021.01) |
| *A61M 60/816* | (2021.01) |
| *A61M 60/829* | (2021.01) |
| *A61M 60/865* | (2021.01) |

(52) U.S. Cl.
CPC ........ *A61M 60/174* (2021.01); *A61M 60/216* (2021.01); *A61M 60/414* (2021.01); *A61M 60/416* (2021.01); *A61M 60/554* (2021.01); *A61M 60/816* (2021.01); *A61M 60/829* (2021.01); *A61M 60/865* (2021.01)

(58) Field of Classification Search
CPC .......... A61B 17/3468; A61B 2017/348; A61B 5/0215; A61M 2025/0024; A61M 2025/0681
See application file for complete search history.

(56) References Cited

U.S. PATENT DOCUMENTS

| | | |
|---|---|---|
| 2006/0041270 A1 | 2/2006 | Lenker et al. |
| 2012/0035585 A1 | 2/2012 | Kurrus et al. |
| 2016/0220741 A1 | 8/2016 | Garrison et al. |
| 2018/0256859 A1 | 9/2018 | Korkuch |
| 2019/0076167 A1 | 3/2019 | Fantuzzi et al. |
| 2019/0110781 A1 | 4/2019 | Walters et al. |
| 2019/0247627 A1 | 8/2019 | Korkuch et al. |

FOREIGN PATENT DOCUMENTS

| | | |
|---|---|---|
| JP | 2019504720 A | 2/2019 |
| KR | 20170032342 A | 3/2017 |
| KR | 20180111977 A | 10/2018 |
| WO | 2009045793 A1 | 4/2009 |
| WO | 2016001439 A1 | 1/2016 |
| WO | 2017137604 A1 | 8/2017 |
| WO | 2019055591 A2 | 3/2019 |

OTHER PUBLICATIONS

Office Action issued in Chinese Patent Application No. 202080041547.X dated Nov. 3, 2023 (18 pp.).
Office Action issued in Indian Patent Application No. 202117051658 dated Jan. 5, 2024 (7 pp.).
Office Action from corresponding Japanese Patent Application No. 2021-562793 dated Jan. 5, 2024.
Office Action issued in Chinese Patent Application No. 202080041547.X dated May 16, 2024 (13 pp.).
Office Action from corresponding Australian Patent Application No. 2020262078 dated Nov. 28, 2024 (5 pp.).
Office Action from corresponding Chinese Patent Application No. 202080041547X dated Nov. 18, 2024 (20 pp.).
Office Action issued in Japanese Patent Application No. 2021-562793 on Sep. 4, 2024 (8 pp.).
Office Action issued in Japanese Patent Application No. 2021-562793 on Mar. 17, 2025 (6 pp.).
Office Action issued in Chinese Patent Application No. 202080041547X dated Feb. 14, 2025 (18 pp.).
Office Action issued in Korean Patent Application No. 10-2021-7038036 dated Apr. 29, 2025 (14 pp.).

* cited by examiner

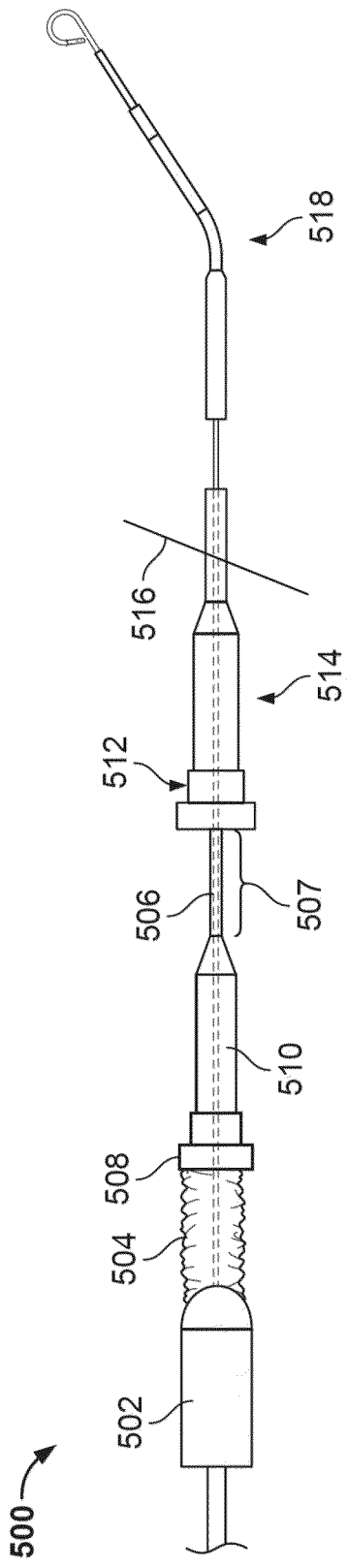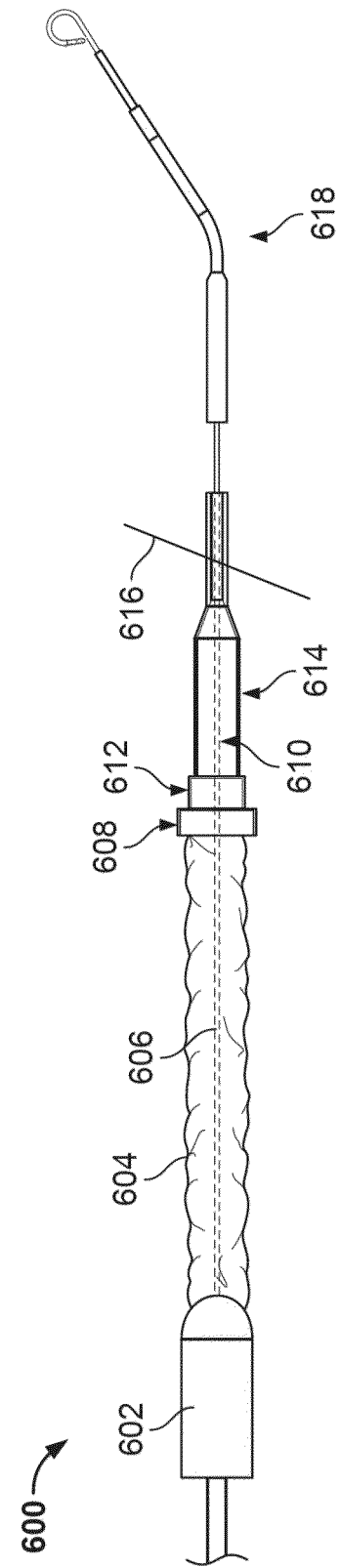

VARIABLE SIZE REPOSITIONING SHEATH

CROSS-REFERENCE TO RELATED APPLICATIONS

The present application is a continuation of U.S. application Ser. No. 16/854,357, filed Apr. 20, 2020, now U.S. Pat. No. 11,911,072 allowed, which application claims priority to U.S. Provisional Application No. 62/836,960, filed Apr. 22, 2019, the disclosures of which are incorporated by reference herein in their entirety.

BACKGROUND

Intracardiac heart pump assemblies may be introduced into the heart either surgically or percutaneously and used to deliver blood from one location in the heart or circulatory system to another location in the heart or circulatory system. For example, when deployed in the heart, an intracardiac pump can pump blood from the left ventricle of the heart into the aorta, or pump blood from the right ventricle to the pulmonary artery. Intracardiac pumps can be powered by a motor located outside of the patient's body or a motor located inside the patient's body. Some intracardiac blood pump systems can operate in parallel with the native heart to supplement cardiac output and partially or fully unload components of the heart. Examples of such systems include the IMPELLA® family of devices (Abiomed, Inc., Danvers MA).

Intracardiac blood pumps such as those just mentioned may be inserted by a catheterization procedure through the femoral artery, femoral vein, or any other suitable path for delivery of the pump to the left or right side of the heart.

In some cases, the intracardiac blood pump may be inserted using an introducer sheath, such as a rigid, fixed diameter sheath, e.g., a peel-away introducer sheath such as the Abiomed Impella CP 14 Fr peel-away sheath. For example, an introducer sheath may be inserted into the femoral artery through an arteriotomy to create an insertion path for a pump assembly. A portion of the pump assembly may then be advanced through an inner lumen of the introducer sheath and into the artery. In order to fit the pump assembly, the inner diameter of a rigid introducer sheath must be large enough to accommodate the largest diameter of the pump assembly, such as the pump head, even if other parts of the pump assembly, such as the catheter, have significantly smaller diameter. In some instances, once the pump assembly has been inserted, the introducer sheath may be removed, e.g., a peel-away introducer sheath may be peeled away. In such cases, a repositioning sheath with a smaller diameter than the introducer sheath may then be advanced over the pump assembly and into the arteriotomy. Replacing the introducer sheath in this way may help to close any annular gap that would otherwise exist between the arteriotomy and the medical device, and reduce limb ischemia and bleeding at the arteriotomy because of the smaller diameter of the repositioning sheath. Moreover, the repositioning sheath may be more easily attached, e.g. via sutures, to the patient, and thus cause less discomfort than a larger introducer sheath.

In other cases, an intracardiac blood pump may be inserted using an expandable introducer sheath. In that regard, an expandable introducer sheath may also be inserted into the femoral artery through an arteriotomy to create an insertion path for a pump assembly. The pump assembly may then be inserted through the expandable introducer sheath, stretching the expandable introducer sheath radially to a diameter large enough to accommodate the largest diameter of the pump assembly. After the pump assembly has been inserted, the expandable introducer sheath may be configured to contract or relax radially to a smaller resting diameter, thereby reducing (compared to a rigid sheath, e.g. a peel-away sheath) the time during which the arteriotomy in the patient's vasculature is stretched to a large diameter, which can cause unwanted bleeding. However, in some instances, expandable introducer sheath assemblies may not include a mechanism to tighten down the expandable sheath on a catheter at a hub of the expandable introducer sheath. Moreover, in some instances, after an expandable introducer sheath relaxes to a resting state, it may leave an annular gap allowing blood to leak between the inner surface of the expandable introducer sheath and the outer surface of the catheter running through the expandable introducer sheath and potentially thrombose in the annular gap. In such cases, a repositioning sheath may also be inserted into the expandable introducer sheath to fill any such annular gaps. Using the repositioning sheath in this way may thus help reduce bleeding and control the flow of blood within the expandable sheath and repositioning sheath. The repositioning sheath may also be configured to be locked in place in a longitudinal direction, thus providing additional stability for long-term support, e.g. in the ICU.

SUMMARY

The present technology relates to systems, devices, and methods for insertion of a device (e.g., intravascular medical device) into a blood vessel using a variable size repositioning sheath.

In one aspect, the disclosure describes a sheath assembly for the insertion of a medical device into a blood vessel comprising an introducer sheath, and a variable size repositioning sheath configured to be inserted into a blood vessel and to be adjustable in size in a radial direction. In some aspects, the variable size repositioning sheath is configured to be adjustable to a radial size that is up to 2 Fr smaller than a radial size of the introducer sheath. In some aspects, the variable size repositioning sheath further comprises a ratchet-type inner repositioning sheath component, and the variable size repositioning sheath is configured to be adjustable in size in a radial direction using the ratchet-type inner repositioning sheath component. In some aspects, the variable size repositioning sheath further comprises a star-shaped inner repositioning sheath component, and the variable size repositioning sheath is configured to be sized in the radial direction using the star-shaped inner repositioning sheath component. In some aspects, the variable size repositioning sheath further comprises a cam-type inner repositioning sheath component, and the variable size repositioning sheath is configured to be sized in the radial direction using the cam-type inner repositioning sheath component. In some aspects, the variable size repositioning sheath further comprises mandrel-type inner repositioning sheath component, and the variable size repositioning sheath is configured to be sized in the radial direction using the mandrel-type inner repositioning sheath component.

In another aspect, the disclosure describes a sheath assembly for the insertion of a medical device into a blood vessel, comprising an expandable introducer sheath, and a variable size repositioning sheath configured to be inserted into the expandable introducer sheath and to be adjustable in size in a radial direction. In some aspects, the variable size repositioning sheath further comprises a ratchet-type inner repositioning sheath component, and the variable size repositioning sheath is configured to be adjustable in size in a radial direction using the ratchet-type inner repositioning sheath component. In some aspects, the variable size repositioning sheath further comprises a star-shaped inner repositioning sheath component, and the variable size repositioning sheath is configured to be sized in the radial direction using the star-shaped inner repositioning sheath component. In some aspects, the variable size repositioning sheath further comprises a cam-type inner repositioning sheath component, and the variable size repositioning sheath is configured to be sized in the radial direction using the cam-type inner repositioning sheath component. In some aspects, the variable size repositioning sheath further comprises mandrel-type inner repositioning sheath component, and the variable size repositioning sheath is configured to be sized in the radial direction using the mandrel-type inner repositioning sheath component.

In another aspect, the disclosure describes a blood pump system, comprising: an intracardiac device comprising a pump and a cannula, the pump having a pump housing, a rotor, and an opening in the pump housing, the cannula having a proximal end that interfaces with a distal end of the pump housing and a distal end with at least one distal opening, the pump being configured to be operated by a motor; an elongate catheter coupled on its distal end to the motor or to the pump housing; and a sheath assembly. The sheath assembly comprises an introducer sheath configured to introduce the intracardiac device into a blood vessel, and a variable size repositioning sheath that is adjustable in a radial direction, the variable size repositioning sheath configured to reposition the intracardiac device inside the blood vessel. In some aspects, the variable size repositioning sheath is configured to be adjustable to a radial size that is up to 2 Fr smaller than a radial size of the introducer sheath. In some aspects, the variable size repositioning sheath further comprises a ratchet-type inner repositioning sheath component, and the variable size repositioning sheath is configured to be adjustable in size in a radial direction using the ratchet-type inner repositioning sheath component. In some aspects, the variable size repositioning sheath further comprises a star-shaped inner repositioning sheath component, and the variable size repositioning sheath is configured to be sized in the radial direction using the star-shaped inner repositioning sheath component. In some aspects, the variable size repositioning sheath further comprises a cam-type inner repositioning sheath component, and the variable size repositioning sheath is configured to be sized in the radial direction using the cam-type inner repositioning sheath component. In some aspects, the variable size repositioning sheath further comprises mandrel-type inner repositioning sheath component, and the variable size repositioning sheath is configured to be sized in the radial direction using the mandrel-type inner repositioning sheath component.

In another aspect, the disclosure describes a sheath assembly for the insertion of a medical device into a blood vessel, comprising a peel-away introducer sheath having a sheath body with a fixed outer diameter, and a variable size repositioning sheath configured to be adjustable in size in a radial direction between at least a first state and a second state, wherein when the variable size repositioning sheath is in the first state, an outer diameter of the variable size repositioning sheath is larger than the fixed outer diameter, and wherein when the variable size repositioning sheath is in the second state, the outer diameter of the variable size repositioning sheath is smaller than the fixed outer diameter. In some aspects, the variable size repositioning sheath further comprises a ratchet-type inner repositioning sheath component, and the variable size repositioning sheath is configured to be adjustable in size in a radial direction using the ratchet-type inner repositioning sheath component. In some aspects, the variable size repositioning sheath further comprises a star-shaped inner repositioning sheath component, and the variable size repositioning sheath is configured to be sized in the radial direction using the star-shaped inner repositioning sheath component. In some aspects, the variable size repositioning sheath further comprises a cam-type inner repositioning sheath component, and the variable size repositioning sheath is configured to be sized in the radial direction using the cam-type inner repositioning sheath component. In some aspects, the variable size repositioning sheath further comprises mandrel-type inner repositioning sheath component, and the variable size repositioning sheath is configured to be sized in the radial direction using the mandrel-type inner repositioning sheath component.

In some aspects of the technology, the medical devices described herein may be delivered through an introducer sheath that is either a fixed size introducer sheath, an expandable introducer sheath, or any other type of sheath. The peel-away introducer sheath may be configured to be removed from an insertion path (e.g., an arteriotomy) after a short duration of time (e.g., <1 hr) and replaced with a variable size repositioning sheath to control of the blood flow in the blood vessel and minimize bleeding. When the introducer sheath is a fixed size introducer sheath, such as a peel-away introducer sheath, the introducer sheath may be removed prior to insertion of the variable size repositioning sheath into the arteriotomy. In such cases, the variable size repositioning sheath may be configured to fill at least part of the annular gap between the arteriotomy and the catheter. For example, after a 14 Fr peel-away sheath has been removed, the arteriotomy may be about 17.9 Fr, as the approximate outer diameter of the 14 Fr peel-away sheath (with 14 Fr inner diameter) is 17.9 Fr. The arteriotomy size may be a function of the diameter of the device that is through it (e.g., 14 Fr peel-away sheath that has approximately a 17.9 Fr outer diameter), the duration that the device is through it, how gradual the dilation of the arteriotomy is, how smooth transitions of the device are, the lubricity of the surface of the introducer sheath during insertion, as well as patient factors such as age, vessel health/elasticity, and vessel disease such as plaque or calcium near the region of access. In some cases, a catheter of the intravascular medical device may have a much smaller outer diameter than the arteriotomy. For example, a catheter may have an outer diameter of about 9 Fr. A variable size repositioning sheath may be sized in a radial direction to fill at least part of the annular gap between the arteriotomy and the catheter, to minimize unwanted bleeding through the annular gap. When the introducer sheath is an expandable introducer sheath, the introducer sheath may be configured to remain in an insertion path (e.g., an arteriotomy) for relatively long durations (e.g., >1 hr, >2 hr, >6 hr, or any suitable duration). If an annular gap is allowed to remain between the expandable introducer sheath and the catheter, it can lead to excessive blood ingress into the annular gap, and allow blood to thrombose in the annular gap. Thrombi in the annular gap is a risk to the patient due to potential migration and eventual embolism. When an expandable introducer sheath cannot seal the arteriotomy (e.g., because it is not stiff enough), the variable repositioning sheath may be inserted to provide a stiffer structure and seal the arteriotomy. Additionally, the expandable introducer sheath may take up a smaller portion of the arteriotomy by itself, and the insertion of the variable size repositioning sheath may expand the sheath such that it takes up a larger portion of the arteriotomy. This may include stretching the arteriotomy to a larger diameter. A variable size repositioning sheath may also be sized to fit (e.g., radially expanded) into the arteriotomy after the peel-away introducer sheath has been removed. For example, a variable size repositioning sheath may be sized to have a 16.9 Fr outer diameter to fit into a 17.9 Fr arteriotomy. A variable size repositioning sheath may also be sized to have an outer diameter to fit into a smaller arteriotomy (e.g., 15.9 Fr) for cases where the repositioning sheath is used with a smaller expandable introducer sheath. Where the variable size repositioning sheath is sized in a radial direction to be slightly smaller than the arteriotomy size, it may be sized based on an acceptable amount of recoil at the arteriotomy, i.e. sized in a radial direction to have a diameter slightly smaller than the arteriotomy size by an amount less than or equal to the acceptable amount of recoil. For example, acceptable recoil may be the amount by which the blood vessel at the arteriotomy is able to contract. As another example, a variable size repositioning sheath may be sized (e.g., radially compressed) to fit into an expandable introducer sheath. The variable size repositioning sheath may be configured to be inserted into the expandable introducer sheath to control blood flow along the expandable sheath, minimize bleeding, and prevent thrombi in the annular gap. For example, a variable size repositioning sheath may be sized to fit into an expandable introducer sheath with a 14 Fr inner diameter and a 15.2 Fr outer diameter. The variable size repositioning sheath may be configured to be continuously adjustable in size in a radial direction over a range of diameters. The variable size repositioning sheath may be configured such that, once it has been adjusted, it will remain in its adjusted state unless it is adjusted again. Additionally, the variable size repositioning sheath may be configured to tighten around the catheter at the hub of the expandable introducer sheath, creating long-term stability and support when using an expandable introducer sheath for an extended period of time. For example, the variable-size repositioning sheath may be fixed relative to a catheter using a device such as a Tuohy-Borst valve.

In some aspects of the technology, the introducer sheaths described herein may be inserted into the femoral artery through an arteriotomy to create an insertion path for the pump assembly. A portion of the pump assembly may then be advanced through an inner lumen of the introducer sheath and into the artery. In some aspects of the technology, the introducer sheath may be a peel-away introducer sheath, such as any peel-away sheath used with any of the Abiomed Impella devices (e.g., the Abiomed Impella CP 14 Fr peel-away sheath). Other standard size peel-away introducer sheaths may have inner diameters of 14 Fr, 16 Fr, 18 Fr, 20 Fr, etc. In some cases, a 14 Fr peel-away sheath may have approximately a 17.9 Fr outer diameter and a 14 Fr inner diameter. Other standard introducer sheaths may include peel-away introducer sheaths with outer diameters of 16.7 Fr, 17.1 Fr, or other sizes between 16.7 Fr and 17.9 Fr. In some cases, the introducer sheath may be an expandable introducer sheath, such as those described in U.S. patent application Ser. No. 16/277,378, published as U.S. Pub. 2019/0247627, the disclosure of which is incorporated by reference herein in its entirety.

In some aspects of the technology, the variable size repositioning sheaths described herein may be configured to be adjusted in size in a radial direction such that they are compatible to be inserted after the removal of a peel-away introducer sheath, or to be inserted into an expandable introducer sheath. The variable size repositioning sheath may have an outer repositioning sheath component and an inner repositioning sheath component. The inner repositioning sheath component and the outer repositioning sheath component may be configured with respective properties (e.g., relative size, shape, material, etc.) such that moving one relative to the other may change the outer diameter of the variable size repositioning sheath (e.g., either radially expanding or radially contracting it). In some cases, the inner repositioning component may be configured to radially expand or contract the outer diameter of the outer repositioning sheath component in response to a translational motion of the inner repositioning sheath component. For example, the variable size repositioning sheath may be configured such that when the inner repositioning component is pushed into the outer repositioning sheath, the outer repositioning sheath moves and an outer diameter of the outer repositioning sheath radially increases in size. Similarly, the variable size repositioning sheath may be configured such that when the inner repositioning component is pulled out of the outer repositioning sheath component, the outer diameter of the repositioning sheath radially decreases in size. In some aspects of the technology, the inner repositioning component may have a cross-section shaped for radially expanding or contracting the size of the outer diameter of the outer repositioning sheath component in response to a rotation of the inner repositioning component. In some aspects, a potential advantage of the technology is that the inner and outer repositioning sheath components may be configured such that moving one relative to the other produces a predictable change of the size and shape of the variable size repositioning sheath along its entire length, whether the variable size repositioning sheath is in its smallest diameter state, largest diameter state, or any state in between.

In some aspects of the technology, the variable size repositioning sheath may include a sizing device for expanding and contracting the radial size of the variable size repositioning sheath. For example, the device may include a ratchet-type or gear-type inner repositioning component, a mandrel-type inner repositioning component, a star-shaped inner repositioning component, a cam-type inner repositioning component, an oval-shaped inner repositioning component, or any other suitable mechanism. The sizing device may be configured to allow an operator (e.g., a physician, medical professional, etc.) to change the radial size of the variable size repositioning sheath by a fixed amount by moving (e.g., through a translational or rotational motion) the inner repositioning sheath component. For example, the operator may control a handle, knob, lever, push device, or any other device connected to a proximal end of the inner repositioning sheath. In some aspects of the technology, an operator may be able to exactly determine how much to move the inner repositioning sheath component because there is a known relationship between the operator's input and the resulting amount of change in the variable size repositioning sheath outer diameter. For example, a clockwise rotational movement of the operator may increase the outer diameter of the variable size repositioning sheath by up to 10 Fr, while a counterclockwise rotational movement of the operator may decrease the outer diameter of the variable size repositioning sheath by up to 10 Fr. Alternatively, for example, a counterclockwise rotational movement of the operator may increase the outer diameter of the variable size repositioning sheath by up to 10 Fr, while a clockwise rotational movement of the operator may decrease the outer diameter of the variable size repositioning sheath by up to 10 Fr. For example, for each 90 degrees of rotational motion imparted by the operator, an outer diameter of the variable size repositioning sheath may increase by 1 Fr. As another example, for each 180 degrees of rotational motion imparted by the operator, an outer diameter of the variable size repositioning sheath may increase by 2 Fr. As another example, for each 90 degrees of rotational motion imparted by the operator, an outer diameter of the variable size repositioning sheath may increase by 0.5 Fr. As another example, for each 90 degrees of rotational motion imparted by the operator, an outer diameter of the variable size repositioning sheath may increase by 0.2 Fr. As another example, for each 90 degrees of rotational motion imparted by the operator, an outer diameter of the variable size repositioning sheath may increase by 0.1 Fr. As another example, for each 90 degrees of rotational motion imparted by the operator, an outer diameter of the variable size repositioning sheath may decrease by 0.1 Fr. As another example, for each 1 mm of translational motion imparted by the operator, an outer diameter of the variable size repositioning sheath may increase by 1 Fr. As another example, for each 1 mm of translational motion imparted by the operator, an outer diameter of the variable size repositioning sheath may increase by 0.5 Fr. As another example, for each 1 mm of translational motion imparted by the operator, an outer diameter of the variable size repositioning sheath may increase by 0.2 Fr. As another example, for each 1 mm of translational motion imparted by the operator, an outer diameter of the variable size repositioning sheath may increase by 0.1 Fr. As another example, for each 1 mm of translational motion imparted by the operator, an outer diameter of the variable size repositioning sheath may decrease by 0.1 Fr. Therefore the relationship between the extent of the motion and the incremental increase or decrease in repositioning sheath diameter is largely a matter of design choice. The relationships described above are by way of example.

In another example, the relationship between the motion imparted by the operator and the resulting amount of change in the variable size repositioning sheath outer diameter may be determined by the operator based on a number of clicks heard or felt by the operator when imparting motion. There may further be a known correspondence between the length or angle between clicks heard or felt by the operator and the resulting change in outer diameter of the variable size repositioning sheath. For example, each click may correspond to a rotation of a set amount of degrees, such as a click every 30 degrees, 45 degrees, 90 degrees, 180 degrees, etc. Feedback indicating the correspondence may be provided to the operator in any form, including haptic feedback, audio feedback, or any other type of notification such that the operator knows the current size of the variable size repositioning sheath corresponding to the motion applied by the operator. In some examples, there may be gradations along the length of the variable size repositioning sheath, where the gradations occur at fixed distances from each other. For example, there may be a gradation every 1 mm, 0.5 mm, 10 mm, or any other fixed amount of distance. Such examples may advantageously allow the operator to know in real-time or near real-time how their actions at a proximal end of the variable size repositioning sheath are affecting or will affect the outer diameter of the variable size repositioning sheath.

In some aspects of the technology, the outer diameter of the variable size repositioning sheath may be radially expanded from a smallest diameter state, or may be radially contracted from a largest diameter state to replace a peel-away introducer sheath after the peel-away introducer sheath has been removed or to fill the annular gap between an expandable introducer sheath and a catheter running through it. Alternatively, the outer diameter of the variable size repositioning sheath may be radially expanded or contracted from an intermediate state with a first diameter to another intermediate state with another diameter. The variable size repositioning sheath may be packaged in the expanded state before being inserted into the arteriotomy after the removal of the peel-away introducer sheath, e.g., to avoid issues that may arise from being stored in a compressed state over a long period of time (e.g., greater than one week, greater than one month, greater than one year, etc.), such as creep of the variable size repositioning sheath when in a compressed state. The variable size repositioning sheath may also be packaged in the contracted state, e.g., to avoid issues that may arise from being stored in an expanded state over a long period of time (e.g., greater than one week, greater than one month, greater than one year, etc.), such as the possibility of plastic deformation of the variable size repositioning sheath, which may prevent an operator from being able to decrease the radial size of the variable size repositioning sheath, the sheath cannot decrease in size.

As noted, in some aspects of the technology, the variable size repositioning sheath may be sized in a radial direction based on an acceptable recoil at the arteriotomy, i.e. a diameter amount by which the blood vessel at the arteriotomy is able to contract. For example, in some cases, a blood vessel at the arteriotomy may be able to recoil to a smaller diameter by about 2 Fr or less. Thus, when using a 14 Fr peel-away introducer sheath having a 17.9 Fr outer diameter, the variable repositioning sheath may be sized to 15.9 Fr to allow for the vessel to recoil by 2 Fr such that the recoiled size of the arteriotomy is about the same as the outer diameter of the repositioning sheath. In some cases, the variable size repositioning sheath may also be configured to allow for further recoil which may take place after the insertion of the variable size repositioning sheath. For example, after a period of time following the insertion of the variable size repositioning sheath (e.g., 15 minutes later, an hour later, a day later, etc.), an operator may decrease the radial size of the variable size repositioning sheath (e.g., decrease the radial size by 2 Fr) to allow for further recoil of the vessel (e.g., to 13.9 Fr). In some cases, the operator may decrease the radial size of the variable size repositioning sheath with multiple adjustments (e.g., decrease the radial size by 1 Fr every 12 hours for a total decrease in the radial size of 4 Fr over 48 hours). The variable size repositioning sheath may also be held fixed to the elongate catheter by using a mechanism such as a Tuohy-Borst valve on a proximal end of the variable size repositioning sheath.

In some aspects of the technology, the variable size repositioning sheath may be sized with a sizing device that may include a ratchet-type or gear-type inner repositioning sheath, a mandrel-type inner repositioning sheath, a star-shaped inner repositioning sheath, a cam-type inner repositioning sheath, or an oval-shaped inner repositioning sheath. The variable size repositioning sheath may be sized in response to a motion by an operator. For example, in response to a rotational or translational motion of a handle, a level, a gear, a tab, or any other equivalent device, the sizing device may convert the motion into a known expansion or contraction of the size of the variable size repositioning sheath. For example, the variable size repositioning sheath may be originally packaged in an expanded state having a 16.7 Fr outer diameter, and be configured such that a 360 degree counter-clockwise rotation of a handle of the variable size repositioning sheath may translate into a 0.1 Fr radial expansion of the outer diameter of the variable size repositioning sheath. In such an example, the operator may thus rotate the handle in a 360 degree counter-clockwise rotation twelve rotations to change the outer diameter size of the variable size repositioning sheath from 16.7 Fr to 17.9 Fr, so that it may fill a 17.9 Fr arteriotomy that is left after a 14 Fr peel-away sheath has been removed.

In some aspects of the technology, the expandable introducer sheaths described herein may be inserted into the femoral artery through an arteriotomy to create an insertion path for the pump assembly. In some cases, the expandable introducer sheath may have a resting outer diameter that is smaller than the fixed outer diameter of a peel-away introducer sheath body. Use of an introducer sheath capable of expansion may allow a smaller size sheath to be used for insertion and may allow the arteriotomy to spend less time at a larger diameter, notwithstanding the sheath being used for longer durations. Additionally, because the pump assembly only momentarily passes through the arteriotomy, the arteriotomy may be smaller than if a larger non-expandable sheath is used. Still further, since the blood pump only momentarily passes through vessel, friction between the intracardiac device, expandable introducer sheath, and vessel wall may be minimized and there may be a reduced axial load and reduced stress on the vessel. That is, the expandable introducer sheath body may be a smaller size and therefore not push or pull the vessel along the axis of the insertion/removal path.

In some aspects of the technology, the variable size repositioning sheath may be configured to be adjusted in size in a radial direction such that an operator of the sheath assembly can choose, depending on whether the operator is using a peel-away introducer sheath or an expandable introducer sheath, a size of the variable size repositioning sheath that is compatible with the type and size of the introducer sheath used. For example, the operator of the sheath assembly may adjust the size of the variable size repositioning sheath in a radial direction to make the variable size repositioning sheath suitable for use after the removal of a peel-away introducer sheath or suitable for use by insertion into an expandable introducer sheath. In some implementations, the variable size repositioning sheath may include a sizing device for expanding and contracting the radial size of the variable size repositioning sheath. For example, the sizing device may be a ratchet-type or gear-type inner repositioning sheath component, a mandrel-type inner repositioning sheath component, a star-shaped inner repositioning sheath component, a cam-type inner repositioning sheath component, or an oval-shaped inner repositioning sheath component.

In some aspects of the technology, the blood pump systems described herein may comprise an intracardiac device including a pump and a cannula, and may be configured to be at least partially inserted within the heart of a patient. For example, the blood pump system may be percutaneously inserted into the heart and run in parallel with the native heart to supplement cardiac output, such as the IMPELLA® family of devices (Abiomed, Inc., Danvers MA). The pump may include a pump housing, a rotor, and an opening in the pump housing. The rotor may be at least partially positioned within the pump housing such that a motor drives the rotor and the rotor pumps blood through the pump housing while the system is operating. The blood pump system may include a cannula with a proximal end that interfaces with the distal end of the pump housing and a distal end with at least one distal opening. The pump may be configured to be placed such that cannula extends across an aortic valve of the patient, the distal end being located within a left ventricle of the patient, and the proximal end being located within an aorta of the patient. Blood may thus flow through the cannula's distal opening, through the body of the cannula, and through the pump housing. In some aspects of the technology, the blood pump may further include a flexible projection extending distally away from the distal end of the cannula, such as a pigtail-shaped flexible projection.

In some aspects of the technology, the blood pump system may further comprise an elongate catheter coupled on its distal end to the motor or to the pump housing. The catheter may connect the pump to a controller or other operating device. In some cases, such a controller may be configured to operate the blood pump system. For example, the controller may be the Automated Impella Controller (AIC) of Abiomed, Inc or any other suitable controller. In some aspects of the technology, the elongate catheter may house electrical connections, connecting the pump to the controller. The blood pump system may further include one or more sensors (e.g., a differential pressure sensor) configured to communicate with the controller or otherwise provide patient health and pump operation data to a clinician or outside device. In some aspects of the technology, a drive cable may extend through the elongate catheter, and may be configured to drive operation of the rotor, e.g., by controlling the speed at which the rotor spins.

In some aspects of the technology, a variable size repositioning sheath may be configured to be sized in the radial direction using a ratchet-type or gear-type inner repositioning sheath component. This may be implemented with any of the aspects described above. For example, a ratchet-type or gear-type inner repositioning sheath component may have any type of gear cross-section with teeth. In some aspects of the technology, the gear may be configured with different sets of teeth that create a fixed change in the size of the variable size repositioning sheath when the inner repositioning sheath component is rotated.

In some aspects of the technology, the variable size repositioning sheath component may be configured to be sized in the radial direction using a cam-type inner repositioning sheath. This may be implemented with any of the aspects described above. The cam-type inner repositioning sheath may be of any cam-type shape, such as round, eccentric, oval, elliptical, hexagonal, star-shaped, etc., such that a rotation of the cam-type inner repositioning sheath component corresponds to an expansion or contraction of the outer diameter of the variable size repositioning sheath.

In some aspects of the technology, the variable size repositioning sheath may be configured to be sized in the radial direction using a mandrel-type inner repositioning sheath component. This may be implemented with any of the aspects described above. The mandrel-type inner repositioning sheath may be configured with a set number of sizes that the mandrel components can radially expand or contract into. For example, the mandrel-type inner repositioning sheath may be configured to expand or contract into five different sizes, where a first of the five sizes corresponds to an outer diameter size for the variable size repositioning sheath that fits into the arteriotomy left from a standard size peel-away introducer sheath (e.g., 17.9 Fr), a second of the five sizes corresponds to an outer diameter size of the variable size repositioning sheath that fits into an expandable introducer sheath (e.g., 14 Fr), and the other three sizes are intermediate sizes between the first and second sizes.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 5 shows a placement system comprising a variable size repositioning sheath inserted into an arteriotomy after an intracardiac device has been inserted through an introducer sheath, according to aspects of the disclosure; and FIG. 6 shows a placement system comprising a variable size repositioning sheath inserted into an arteriotomy after an intracardiac device has been inserted through an introducer sheath, according to aspects of the disclosure.

DETAILED DESCRIPTION

Figures 1, 2:
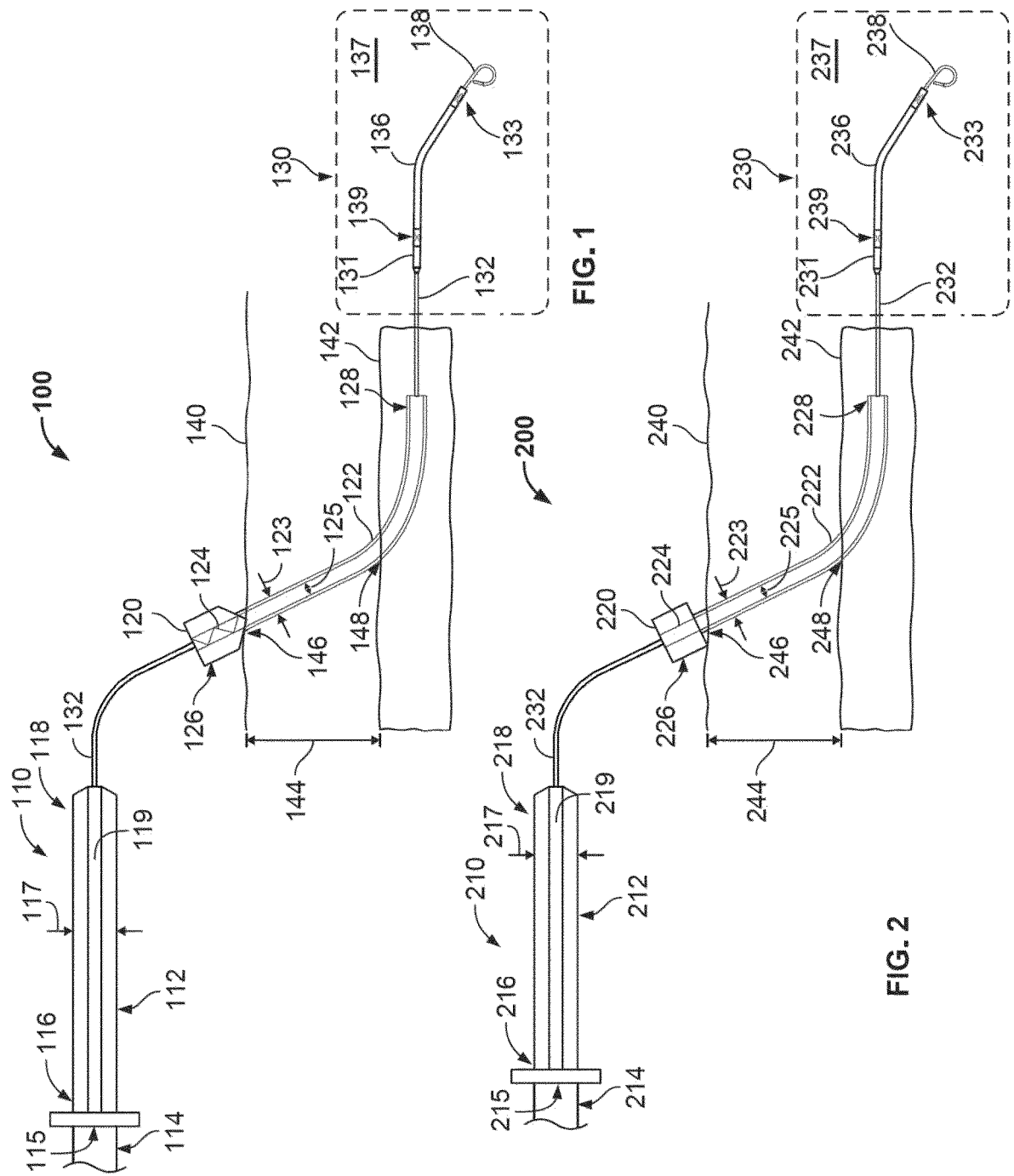
FIG. 1 shows a placement system comprising a peel-away introducer sheath configured to introduce an intracardiac device into a patient's vasculature and a variable size repositioning sheath sized in the radial direction for insertion into the arteriotomy after the removal of the peel-away introducer, according to aspects of the disclosure.
FIG. 2 shows a placement system comprising an expandable introducer sheath configured to introduce an intracardiac device into a patient's vasculature and a variable size repositioning sheath sized in the radial direction for insertion into the expandable introducer sheath, according to aspects of the disclosure.

To provide an overall understanding of the systems, methods, and devices described herein, certain illustrative examples will be described. Although the examples and features described herein are specifically described for use in connection with an intracardiac heart pump system, it will be understood that all the components and other features outlined below may be combined with one another in any suitable manner and may be adapted and applied to other types of medical devices such as electrophysiology study and catheter ablation devices, angioplasty and stenting devices, angiographic catheters, peripherally inserted central catheters, central venous catheters, midline catheters, peripheral catheters, inferior vena cava filters, abdominal aortic aneurysm therapy devices, thrombectomy devices, TAVR delivery systems, cardiac therapy and cardiac assist devices (including balloon pumps), cardiac assist devices implanted using a surgical incision, and any other venous or arterial based introduced catheters and devices.

The systems and methods described herein provide a sheath assembly for the insertion of a medical device (e.g., an intracardiac heart pump) into a blood vessel through a vessel aperture. The sheath assembly may comprise an introducer sheath and a variable size repositioning sheath. The introducer sheath may include a peel-away introducer sheath or an expandable introducer sheath. The variable size repositioning sheath may be adjustable in size in a radial direction such that its diameter may be adjusted over a certain range. In some aspects, the adjustment range of a variable size repositioning sheath may include a diameter suitable for allowing insertion of the variable size repositioning sheath into an introducer sheath.

Repositioning sheaths are sometimes packaged with intracardiac devices with a catheter passing through the repositioning sheath, such that the repositioning sheath and the catheter share the same longitudinal central axis. Generally, the repositioning sheaths of existing systems have a diameter that cannot be significantly changed. In that regard, though a fixed-size repositioning sheath may have a diameter that tapers in a longitudinal direction, the diameter cannot be adjusted prior to use. Accordingly, to use a fixed-size repositioning sheath, the repositioning sheath must be moved in a longitudinal direction relative to the catheter, and into the arteriotomy before being locked in place. Because the size of the arteriotomy can vary greatly depending on the patient or procedure, a repositioning sheath with a fixed size or fixed diameter may be not always be effective in occluding the annular gap between the arteriotomy and the catheter to prevent large leaks and reduce the risk of limb ischemia.

Advantageously, a variable size repositioning sheath's adjustability in size in the radial direction may aid in insertion into a blood vessel, the size of which may vary depending on patient characteristics (e.g. age, medical condition) or procedure characteristics (e.g. length, complexity, instruments used). In addition, as repositioning sheaths are often packaged together with an intracardiac device, and with a catheter running through the repositioning sheath, this can prevent an operator from swapping out the packaged repositioning sheath for a different size repositioning sheath. However, where a variable size repositioning sheath is included instead of a repositioning sheath with a fixed diameter, the variable size repositioning sheath may be packaged at a given size and adjusted in size by the operator immediately prior to (or simultaneously with) sliding the repositioning sheath in place through the arteriotomy. This adjustment may be done, for example, to enable the repositioning sheath to fill at least part of an annular gap between the arteriotomy and an elongate catheter, which can also vary in size depending on patient characteristics and/or procedure characteristics.

A variable size repositioning sheath having an adjustable diameter may be configured to be compatible with both a peel-away introducer sheath and an expandable-size repositioning sheath. For example, after a 14 Fr peel-away introducer sheath has been removed, the diameter of the arteriotomy may be about 17.9 Fr due to the 17.9 Fr effective outer diameter of the 14 Fr peel-away introducer sheath. In addition, an elongate catheter may have an outer diameter of about 9 Fr. Thus, in some aspects of the technology, replacing a peel-away introducer sheath by a variable size repositioning sheath may help to fill at least part of the annular gap, minimizing unwanted bleeding through the annular gap. In addition, in some aspects of the technology, a variable size repositioning sheath may be fixed relative to an elongate catheter using a device such as a Tuohy-Borst valve.

In some aspects of the technology, peel-away introducer sheaths may be inserted into the femoral artery through an arteriotomy to create an insertion path for the pump assembly. In such cases, a portion of the pump assembly may then be advanced through an inner lumen of the peel-away introducer sheath and into the artery. Once the pump assembly has been inserted, the introducer sheath may then be peeled away, and a variable-size repositioning sheath may then be advanced over the pump assembly and into the arteriotomy.

In some aspects of the technology, as an alternative to a peel-away introducer sheath, an expandable introducer sheath may be inserted into the femoral artery through an arteriotomy to create an insertion path for a pump assembly. In such cases, a portion of the pump assembly may then be advanced through an inner lumen of the expandable introducer sheath and into the artery, where the expandable sheath body may expand and contract between different states to accommodate the medical device. For example, the expandable introducer sheath body may be elongated and have a first smaller diameter state for insertion of the introducer sheath body into the arteriotomy, and may then be shortened or allowed to relax into a second larger diameter state once at a desired location. The second larger diameter state may be configured to allow the passage of a portion of a medical device through the inner lumen of the introducer sheath, the portion of the medical device having a transverse cross-sectional area larger than a transverse cross-sectional area of the inner lumen in the first smaller diameter state. In some aspects of the technology, the introducer sheath may be further expanded from a resting state when the sheath is at its desired location, to a larger diameter state when the medical device is passed through the introducer sheath.

FIG. 1 shows a placement system 100 comprising a peel-away introducer 120 configured to introduce an intracardiac device 130 into a patient's vasculature and a variable size repositioning sheath 110 sized in the radial direction for insertion into the arteriotomy 148 after the removal of the peel-away introducer 120, according to aspects of the disclosure. The placement system 100 includes variable size repositioning sheath 110, peel-away introducer sheath 120 and intracardiac device 130. FIG. 1 shows an exemplary positioning of peel-away introducer 120 with intracardiac device 130 having been inserted through peel-away introducer sheath 120 and positioned such that the intracardiac device 130 has entered the patient's vasculature.

In the example of FIG. 1, the intracardiac device 130 comprises a pump 137. Pump 137 comprises a cannula 136, a pump housing 139 with proximal openings, a rotor (not shown), and distal cage 133 with distal openings. In all cases herein, the operator (not the patient) is used as the point of reference, such that "proximal" refers to a direction pointing toward the operator or a position closer to the operator, and "distal" refers to a direction pointing away from the operator or a position farther from the operator. The pump is configured to be operated by a motor within motor housing 131. Elongate catheter 132 is coupled on its distal end to the motor housing 131. Elongate catheter 132 defines a central lumen therein. In some aspects of the technology, elongate catheter 132 may be coupled to pump housing 139. The proximal end of cannula 136 interfaces with the distal end of the pump housing 139. The distal end of cannula 136 interfaces with distal cage 133, which defines distal openings. Cannula 136 defines a lumen therein. In some aspects of the technology, blood may be pumped through cannula 136 in the proximal direction such that the proximal openings of pump housing 139 serve as blood outflow ports and the distal openings of distal cage 133 serve as blood inflow ports. In some aspects of the technology, blood may be pumped through cannula 136 in the distal direction such that the proximal openings of pump housing 139 serve as blood inflow ports and the distal openings of distal cage 133 serve as blood outflow ports. A flexible tip 138 may be attached to the distal end of the distal cage 133. In some aspects of the technology, the central lumen of elongate catheter 132 and the lumen of cannula 136 may together define a lumen through the intracardiac device 130 for use in delivering purge fluid during operation of the device.

In some aspects of the technology, the motor of pump 137 may be "onboard," as shown in FIG. 1, and may be located within the patient's body during operation and may include electrical leads that transmit power to the motor for driving pump 137. In some aspects of the technology, the motor of pump 137 may be located outside of the patient's body and may actuate the rotor via a drive shaft, drive cable, or drive line. For example, the motor of pump 137 may be located within a handle (not shown) of the intracardiac device 130. In some aspects of the technology, a drive cable may extend through elongate catheter body 132 to a rotor located near a proximal end of cannula 136.

Peel-away introducer sheath 120 comprises a hub 124 and a peel-away introducer sheath body 122. The peel-away introducer sheath body 122 is defined by a distal end 128, a proximal end 126, and a lumen extending through the sheath body 122 between the proximal and distal ends. On the proximal end 126, the hub 124 is attached to the peel-away introducer sheath body 122. There is a hemostasis valve (not shown) within the hub 124 that allows for the insertion of components through the hub 124 and into the sheath body 122 while preventing fluid (e.g., blood) within the sheath body 122 from escaping through hub 124.

Peel-away introducer sheath body 122 has a fixed, predetermined outer diameter 123 and predetermined inner diameter 125. Both the inner and outer diameters are fixed along the entire length of the introducer sheath body 122. At the distal end 128 of the introducer sheath body 122 is a tip. In some aspects of the technology, the tip at distal end 128 is tapered and has an inner diameter and outer diameter. In some aspects, the taper may be linear for both the inner diameter and the outer diameter. Where peel-away introducer sheath 122 is not radially expandable, the inner diameter 125 must be large enough to accommodate the largest diameter of the intracardiac device 130 (e.g., such as the pump head), even if other parts of the pump assembly (e.g., the catheter) have a significantly smaller diameter. Once the intracardiac device 130 has been positioned in the patient's vasculature as shown in FIG. 1, peel-away introducer 120 may be peeled apart and removed from the patient (e.g., by peeling the peel-away introducer 120 along axial notches or scorings thereon that allow the sheath to be torn axially). In some aspects of the technology, the peel-away introducer sheath 120 may have a sheath body with a 14 Fr inner diameter and a 17.9 Fr outer diameter, and may leave an approximately 17.9 Fr opening at the arteriotomy 148 in blood vessel 142 and/or at the insertion site 146 of skin 140 after the peel-away introducer sheath 120 is removed.

Variable size repositioning sheath 110 comprises a hub 114 and variable size repositioning sheath body 112. The variable size repositioning sheath body 112 is defined by a distal end 118, a proximal end 116, and a lumen 119 extending through the sheath body 112 between the proximal and distal ends. The distal end of the hub 114 is attached to the proximal end 116 of variable size repositioning sheath body 112. Hub 114 includes a sizing device 115 that is configured to adjust the outer diameter 117 of variable size repositioning sheath body 112. In some aspects of the technology, an operator may adjust the outer diameter 117 by moving (e.g., pressing, toggling, twisting, etc.) the proximal end of sizing device 115. For example, a translational motion or a rotational motion may cause a radial expansion or a radial contraction of the outer diameter 117 of variable size repositioning sheath body 112. Various potential configurations of sizing device 115 are discussed in detail with respect to the examples of FIGS. 3A-3C and 4A-4F. Although FIG. 1 shows the outer diameter 117 of variable size repositioning sheath body 112 being larger than the outer diameter 123 of peel-away introducer sheath body 122, the diagram of FIG. 1 is not meant to show relative dimensions, and outer diameter 117 may be smaller than, equal to, or larger than outer diameter 123.

In some aspects of the technology, the variable size repositioning sheath hub 114 may be configured to lock into the introducer sheath hub 124 using a locking mechanism of any suitable type. For example, the variable size repositioning sheath hub 114 may lock into the introducer sheath hub 124 using a locking pin, a clamp, a twist lock, a pop lock, a snapping fit, etc. In some aspects of the technology, the locking mechanism may be further configured to allow the variable size repositioning sheath hub 114 to be rotated with respect to the introducer sheath hub 124 when the two are locked together.

In some aspects of the technology, the variable size repositioning sheath 110 may be part of a larger assembly such as a repositioning unit or a guide wire repositioning unit.

In some aspects of the technology, the intracardiac device 130 may be inserted into the femoral artery through an arteriotomy to create an insertion path for the pump assembly. A portion of the pump assembly may then be advanced through an inner lumen of the peel-away introducer sheath 120 and into the artery (e.g., blood vessel 142). Once the pump assembly 137 has been inserted, the introducer sheath 120 may be peeled away. After removing the peel-away introducer sheath 120, variable size repositioning sheath 110 may then be advanced, for example, into the arteriotomy to take the place of the removed peel-away introducer sheath 120. Replacing the peel-away introducer sheath 120 with a variable size repositioning sheath 110 having a smaller outer diameter than the outer diameter of the peel-away introducer sheath 120 may reduce limb ischemia and bleeding at the arteriotomy. After the removal of the peel-away repositioning sheath 120, there may be an annular gap between the arteriotomy 148 and the outer surface of the elongate catheter 132, which may lead to bleeding at the arteriotomy 148, and potentially the insertion site 146 as well. The insertion of the variable size repositioning sheath 110 may be used to fill the annular gap and prevent bleeding, while still allowing the arteriotomy 148 to undergo an acceptable amount of recoil (e.g., about 0 to about 2 Fr). In addition, in some aspects of the technology, variable size repositioning sheath 110 may be configured to be affixed to the patient, e.g. using sutures, to prevent movement of the variable size repositioning sheath 110 relative to the elongate catheter 132 and the potential for patient discomfort. In order to allow arteriotomy 148 of blood vessel 142 to recoil some while still avoiding an annular gap that may allow bleeding, the outer diameter 117 of variable size repositioning sheath body 112 may be adjusted such that it is within a range of about 0 to about 2 Fr of the outer diameter 123 of peel-away introducer sheath body 122. For example, if peel-away introducer sheath body 122 results in an arteriotomy 148 of 17.9 Fr, then the outer diameter 117 of variable size repositioning sheath body 112 may be set using sizing device 115 to be no smaller than 15.9 Fr and no larger than 17.9 Fr. In some aspects of the technology, this adjustment of the outer diameter 117 of variable size repositioning sheath body 112 may be done before the distal end 118 of the variable size repositioning sheath 110 is advanced into the arteriotomy 148 or simultaneous therewith. In some aspects, the outer diameter 117 of variable size repositioning sheath body 112 may be adjusted (or readjusted) after the distal end 118 of variable size repositioning sheath 110 has been inserted into the arteriotomy 148.

In some aspects of the technology, the variable size repositioning sheath 110 may be packaged in an expanded state to avoid issues that may arise from being stored in a compressed state, such as creep of the variable size repositioning sheath 110 when in a compressed state. For example, the variable size repositioning sheath 110 may deform when held in a compressed state for over a long period of time (e.g. great than about one week, greater than about one month, greater than about one year, etc.). However, the variable size repositioning sheath 110 may also be packaged in a compressed state or a neutral state where creep is not a concern, and/or where other considerations make doing so preferable.

In some aspects of the technology, the variable size repositioning sheath 110 may be packaged in a state such that the outer diameter 117 is less likely to need to be adjusted before being advanced into the arteriotomy 148 after the removal of the peel-away introducer sheath 120. For example, where variable size repositioning sheath 110 is packaged with, or expected to be used with, a peel-away introducer sheath 120 having an outer diameter 123 of 17.9 Fr, variable size repositioning sheath 110 may be packaged in an expanded state such that its outer diameter 117 is preset using sizing device 115 to a value between 15.9 Fr and 17.9 Fr (or some other range, if recoil of arteriotomy 148 is expected to be more or less than 0-2 Fr). However, in some aspects, the variable size repositioning sheath 110 may be packaged in a state where it needs to be expanded or contracted using sizing device 115 in order to be sized appropriately for insertion into arteriotomy 148.

The size of the variable size repositioning sheath 110 may be adjusted on a patient-by-patient basis, as the inner diameter of blood vessel 142, the distance 144 between skin 140 and blood vessel 142, the size of the arteriotomy 148, and the amount of recoil in the arteriotomy 148, may all vary on a patient-by-patient basis. As such, sizing device 115 may be used to adjust the outer diameter 117 of variable size repositioning sheath body 112 to be smaller or larger depending on these patient-specific characteristics.

In addition, an operator placing a pump into a patient using a sheath assembly may choose to use either a peel-away introducer sheath such as the ones shown in FIG. 1 and described above, or an expandable introducer sheath such as those shown in FIG. 2 and described below. An operator's selection of which type of introducer sheath to use may be based in part on their experience or familiarities with each type of introducer sheath, the type of procedure, and/or patient anatomy. As will be discussed further below, the variable size repositioning sheaths disclosed herein may be used with expandable introducer sheaths as well.

FIG. 2 shows a placement system 200 comprising an expandable introducer 220 configured to introduce an intracardiac device 230 into a patient's vasculature and a variable size repositioning sheath 210 sized in the radial direction for insertion into the expandable introducer sheath 220, according to aspects of the disclosure. The variable size repositioning sheath 210 is the same type as the variable size repositioning sheath 110 shown and described with of FIG. 1. The placement system 200 includes variable size repositioning sheath 210, expandable introducer sheath 220 and intracardiac device 230. FIG. 2 shows an exemplary positioning of expandable introducer 220 with intracardiac device 230 having been inserted through expandable introducer sheath 220 and positioned such that the intracardiac device 230 enters the patient's vasculature.

In the example of FIG. 2, the intracardiac device 230 comprises a pump 237. Pump 237 comprises a cannula 236, a pump housing 239 with proximal openings, a rotor (not shown), and distal cage 233 with distal openings. The pump is configured to be operated by a motor within motor housing 231. Elongate catheter 232 is coupled on its distal end to the motor housing 231. Elongate catheter 232 defines a central lumen therein. In some aspects of the technology, elongate catheter 232 may be coupled to pump housing 239. The proximal end of cannula 236 interfaces with the distal end of the pump housing 239. The distal end of cannula 236 interfaces with distal cage 233, which defines distal openings. Cannula 236 defines a lumen therein. In some aspects of the technology, blood may be pumped through cannula 236 in the proximal direction such that the proximal openings of pump housing 239 serve as blood outflow ports and the distal openings of distal cage 233 serve as blood inflow ports. In some aspects of the technology, blood may be pumped through cannula 236 in the distal direction such that the proximal openings of pump housing 239 serve as blood inflow ports and the distal openings of distal cage 233 serve as blood outflow ports. A flexible tip 238 may be attached to the distal end of the distal cage 233. In some aspects of the technology, the central lumen of elongate catheter 232 and the lumen of cannula 236 may together define a lumen through the intracardiac device 230 for use in delivering purge fluid during operation of the device.

In some aspects of the technology, the motor of pump 237 may be "onboard," as shown in FIG. 2, and may be located within the patient's body during operation and may include electrical leads that transmit power to the motor for driving pump 237. In some aspects of the technology, the motor of pump 237 may be located outside of the patient's body and may actuate the rotor via a drive shaft, drive cable, or drive line. For example, the motor of pump 237 may be located within a handle (not shown) of the intracardiac device 130. In some aspects of the technology, a drive cable may extend through elongate catheter body 232 to a rotor located near a proximal end of cannula 236.

Expandable introducer sheath 220 comprises a hub 224 and an expandable introducer sheath body 222. The expandable introducer sheath body 222 is defined by a distal end 228, a proximal end 226, and a lumen extending through sheath body 222 between the proximal and distal ends. On the proximal end 222, the hub 224 is attached to the expandable introducer sheath body 222. On the proximal side of the hub 224, there is a hemostasis valve (not shown) within the hub 224. Such hemostasis valve within the hub 224 may allow for the insertion of components through the hub 224 and into the sheath body 222 while preventing fluid (e.g., blood) within the sheath body 222 from escaping through hub 224. The distal end 228 of the expandable introducer sheath body 222 may also be configured to be atraumatic, so as to prevent or minimize the risk of damaging the blood vessel wall or any other anatomy during insertion and/or while the expandable introducer sheath body 222 remains within a patient.

Expandable introducer sheath body 222 has an expandable outer diameter 223 and inner diameter 225. The expandable outer diameter 223 of expandable introducer sheath body 222 may be smaller when in a relaxed state than the fixed outer diameter 123 of peel-away introducer sheath body 122. Use of an introducer sheath capable of expansion allows the size of the sheath body to be smaller during insertion and after a medical device has been passed through it into the blood vessel. As a result, an expandable introducer sheath may allow the blood vessel and arteriotomy to spend less time at a larger diameter than it would with a fixed-size peel-away sheath, even in cases where the expandable introducer sheath is left in the patient for a longer duration than a peel-away sheath. This may allow the expandable introducer sheath to cause less damage to the blood vessel and tissue than a fixed-diameter introducer sheath, e.g. a peel-away introducer sheath. In that regard, the outer diameter 223 of expandable introducer sheath body 222 may be smaller at rest than a maximum outer diameter of the intracardiac device 230, and may expand to a larger diameter when the intracardiac device is passing through the expandable introducer sheath body 222. Likewise, the expandable introducer sheath body 222 may be configured to relax or recoil such that its outer diameter 223 returns to a smaller resting state after the largest portion (s) of the intracardiac device 230 have passed through the expandable introducer sheath body 222. This also allows blood vessel 242, arteriotomy 248, and insertion site 246 to recoil to a smaller and more natural diameter after the largest portion(s) of the intracardiac device 230 have passed through the expandable introducer sheath body 222. Moreover, because intracardiac device 230 only momentarily passes through the vessel wall at arteriotomy 248, it may recoil to a smaller size than would be the case with a fixed-diameter sheath. In addition, also because the intracardiac device 230 only momentarily passes through vessel 242, friction between the intracardiac device 230, expandable introducer sheath body 222, and vessel wall may be reduced, and there may also be reduced axial load and reduced stress on vessel 242 (relative to a fixed-diameter introducer sheath). That is, in a relaxed or rest state where no forces are applied to it, the expandable introducer sheath body 222 may have a smaller diameter than a fixed-diameter introducer sheath body (e.g., peel-away introducer sheath body 122) and therefore may not push or pull the vessel 242 and/or the arteriotomy 248. In addition, when the intracardiac device 230 passes through expandable introducer sheath body 222, the vessel 242 and arteriotomy 248 will simply be expanded outward radially.

The expandable introducer sheath body 222 may have any suitable structure. In some aspects of the technology, the expandable introducer sheath body 222 may have a structure comprised of a frame and one or more coatings, or other configurations as described in U.S. patent application Ser. No. 16/277,378, published as U.S. Pub. 2019/0247627, which has been incorporated by reference herein. For example, the frame may include a plurality of strands extending longitudinally between a proximal end and a distal end of the frame. The frame may also include a smooth coating about the exterior surface and protrusions extending into the lumen along the inner surface. In some aspects of the technology, the frame may be comprised of at least one of the following materials: Nitinol round wire; Nitinol flat wire; stainless steel round wire; stainless steel flat wire; liquid crystal polymer; polyamide; polyether ether ketone (PEEK); polyethylene; or polytetrafluoroethylene (PTFE). In some aspects, the frame may have a braided configuration. In some aspects, the frame may be encapsulated by at least one of the following polymers: silicone; thermoplastic polyurethane; styrenic block copolymer (SBC); an elastomer, including a thermoplastic elastomer (TPE); fluorinated ethylene propylene (FEP); or cyclic olefin copolymer (COC). A frame and encapsulating material combination such as those just described may permit the sheath body 222 to expand and contract while retaining sufficient rigidity to maintain an open lumen and withstand axial forces when the medical device is inserted or withdrawn, and may further promote a smooth flow of blood along the outer surface of the sheath to reduce the risk of clots (thrombi) forming.

Variable size repositioning sheath 210 comprises a hub 214 and variable size repositioning sheath body 212. The variable size repositioning sheath body 212 is defined by a distal end 218, a proximal end 216, and a lumen 219 extending through the sheath body 212 between the proximal and distal ends. The distal end of the hub 214 is attached to the proximal end 216 of variable size repositioning sheath body 212. Hub 214 includes a sizing device 215 that is configured to adjust the outer diameter 217 of variable size repositioning sheath body 212. In some aspects of the technology, an operator may adjust the outer diameter 217 by moving (e.g., pressing, toggling, twisting, etc.) the proximal end of sizing device 215. For example, a translational motion or a rotational motion may cause a radial expansion or a radial contraction of the outer diameter 217 of variable size repositioning sheath body 212. Various potential configurations of sizing device 215 are discussed in detail with respect to the examples of FIGS. 3A-3C and 4A-4F. Although FIG. 2 shows the outer diameter 217 of variable size repositioning sheath body 212 being larger than the outer diameter 223 of expandable introducer sheath body 222, the diagram of FIG. 2 is not meant to show relative dimensions, and outer diameter 217 may be smaller than, equal to, or larger than outer diameter 223.

In some aspects of the technology, variable size repositioning sheath body 210 may be inserted into the expandable introducer sheath 220. For example, the variable size repositioning sheath body 212 may be passed over elongate catheter 232, through hub 224 of expandable introducer 220, and into expandable introducer sheath body 222. The variable size repositioning sheath body 212 may then be advanced through expandable introducer sheath body 222 until the distal end 218 of variable size repositioning sheath body 212 has moved past arteriotomy 228. Inserting the variable size repositioning sheath 210 into the expandable introducer sheath 220 in this way may allow the variable size repositioning sheath 220 to be used to fill some or all of any annular gap that may exist between the inner surface of the expandable introducer sheath body 222 and the outer surface of the elongate catheter 232, as well as any annular gap that may exist between arteriotomy 248 and the outer surface of the expandable introducer sheath body 222. Inserting the variable size repositioning sheath 210 into the expandable introducer sheath 220 may also provide stability and prevent kinking within the expandable introducer sheath body 222.

Depending on the needs of the operator, prior to or simultaneous with inserting variable size repositioning sheath 210 into expandable introducer 220, the outer diameter 217 of the variable size repositioning sheath body 212 may be adjusted using sizing device 215 to be smaller than, the same as, or larger than the inner diameter 225 of the expandable introducer sheath body 222 in its relaxed state. For example, in some aspects of the technology, the expandable introducer sheath body 222 may have an outer diameter 223 of approximately 15.9 Fr and an inner diameter 225 of approximately 14.7 Fr, and the outer diameter 217 of the variable size repositioning sheath body 212 may be adjusted to be smaller than the 14.7 Fr. Likewise, in some aspects of the technology, the outer diameter 217 of the variable size repositioning sheath body 212 may be adjusted to be as large as, or larger than, the largest section of the intracardiac device 230 (e.g., between 5.05 mm and 5.25 mm, if intracardiac device 230 is one of the Abiomed Impella devices, such as the Impella CP pump). In addition, in some aspects of the technology, the outer diameter 217 of the variable size repositioning sheath body 212 may be adjusted (or readjusted) after the variable size repositioning sheath 210 has been inserted into the expandable introducer 220.

In some aspects of the technology, the variable size repositioning sheath 210 may further be configured such that it can be clamped or tightened down on the elongate catheter 232 to prevent or limit relative motion between the two in a longitudinal direction. For example, the variable size repositioning sheath 210 may be fixed to the elongate catheter 232 with a device such as a Tuohy-Borst valve, which may be arranged within or proximate to hub 214. In some aspects of the technology, the variable size repositioning sheath 210 may be configured to be attached, e.g. via sutures, to the patient, thus preventing or limiting relative motion between the variable size repositioning sheath 210 and the patient, and, when clamped, between the elongate catheter 232 and the patient.

In some aspects of the technology, the variable size repositioning sheath 210 may be packaged in an expanded state to avoid issues that may arise from being stored in a compressed state, such as creep of the variable size repositioning sheath 210 when in a compressed state. For example, the variable size repositioning sheath 210 may deform when held in a compressed state for over a long period of time (e.g. greater than about one week, greater than about one month, greater than about one year, etc.). However, the variable size repositioning sheath 210 may also be packaged in a compressed state or a neutral state where creep is not a concern, and/or where other considerations make doing so preferable.

In some aspects of the technology, the variable size repositioning sheath 210 may be packaged such that it is less likely to need to be adjusted if it is used with an expandable introducer sheath 220. For example, where variable size repositioning sheath 210 is packaged with, or expected to be used with, an expandable introducer sheath 220 having an inner diameter 225 of 14.7 Fr when at rest, variable size repositioning sheath 210 may be packaged in a state such that its outer diameter 217 is preset using sizing device 215 to a value less than or equal to 14.7 Fr. However, in some aspects, the variable size repositioning sheath 210 may be packaged in a state where it needs to be expanded or contracted using sizing device 215 in order to be sized appropriately for insertion into expandable introducer sheath 220. For example, in some aspects of the technology, the variable size repositioning sheath 210 may be packaged in a state such that the outer diameter 217 is less likely to need to be adjusted if it is used with a standard peel-away introducer sheath, as discussed above in connection with FIG. 1. In such a case, even if the variable size repositioning sheath 210 is ultimately used instead in combination with an expandable introducer sheath such as shown in FIG. 2, the operator can simply actuate the sizing device 215 of the variable size repositioning sheath 210 to configure the size of the variable size repositioning sheath body 212 according to their particular needs.

The size of the variable size repositioning sheath 210 may be adjusted on a patient-by-patient basis, as the inner diameter of blood vessel 242, the distance 244 between skin 240 and blood vessel 242, the size of the arteriotomy 248, the amount of recoil in the arteriotomy 248, and the annular gap between the outer surface of elongate catheter 232 and the inner surface of expandable introducer sheath body 222, may all vary on a patient-by-patient basis. As such, sizing device 215 may be used to adjust the outer diameter 217 of variable size repositioning sheath 210 to be smaller or larger depending on these patient-specific characteristics.

Figure 3A:
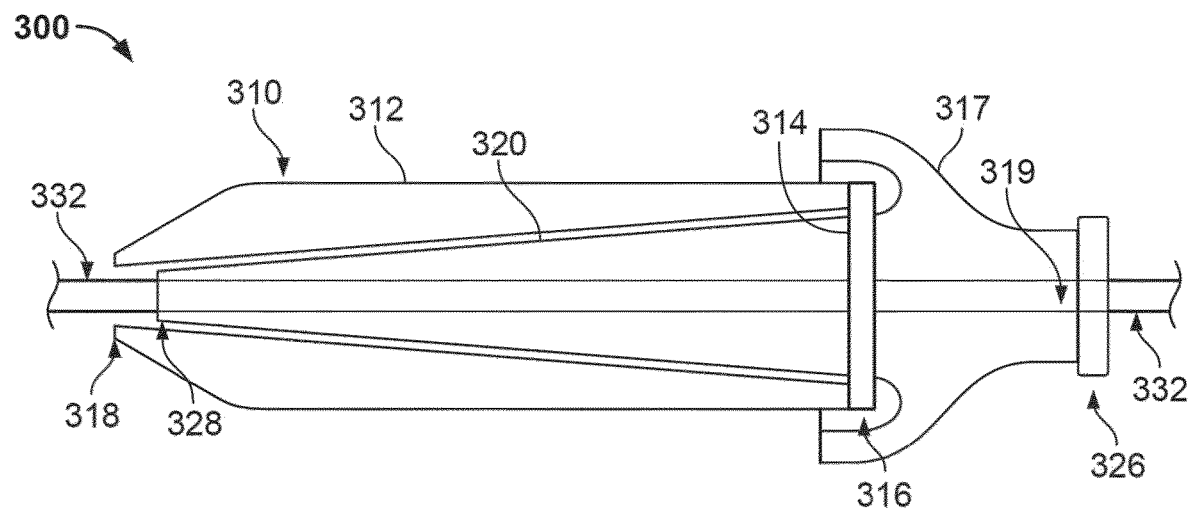
FIG. 3A shows a cross-sectional view of an example sizing device according to aspects of the disclosure.

FIG. 3A depicts an example sizing device configured to expand or contract a size of a variable size repositioning sheath, according to aspects of the technology. In that regard, sizing device 300 comprises variable size repositioning sheath 310 that includes an outer repositioning sheath component 312 with hub 314, inner repositioning sheath component 320, and handle 317. The outer repositioning sheath component 312 includes a distal end 318, a proximal end 316, and a tapered cavity or lumen extending therethrough between the proximal and distal ends. The inner repositioning sheath component 320 is disposed within the tapered cavity or lumen of outer repositioning sheath component 312. The outer surface of the portion of the inner repositioning sheath component 320 that is disposed within outer repositioning sheath component 312 is also tapered linearly. Inner repositioning sheath 320 comprises a distal end 328, a proximal end 326, and a lumen 319 extending therethrough between the proximal and distal ends, such that elongate catheter 332 may be inserted through lumen 319. A handle 317 is arranged at the proximal end 326 of inner repositioning sheath component 320. In some aspects of the technology, handle 317 may be replaced with a level, tab, gear, or any other device suitable for moving inner repositioning sheath component 320.

In some aspects of the technology, the inner repositioning sheath component 320 may be more rigid than the outer repositioning sheath component 312. In some aspects of the technology, the inner repositioning sheath component 320 may be reinforced with a sleeve of a different material. For example, the inner repositioning sheath component 320 may be a polymer and it may be reinforced with a metal sleeve. In some aspects of the technology, the inner repositioning sheath component 320 may be made of a material with a greater strength than the outer repositioning sheath component 312. In some aspects of the technology, the inner repositioning sheath component 320 may comprise a metal frame. Allowing inner repositioning sheath component 320 to be more rigid than the outer variable size repositioning sheath component 312 may help to prevent or limit deformation of the inner repositioning sheath component 320 when it acts on the outer repositioning sheath component 312 to expand or contract the outer diameter of the variable size repositioning sheath 310.

The sizing devices described herein (e.g., sizing device 300, sizing device 400) may be configured such that inner repositioning component acts on outer repositioning sheath component to expand or contract the variable size repositioning sheath in a continuous manner, or in discrete increments. In some aspects of the technology, the sizing devices described herein may be configured so that the operator can determine how much the variable size repositioning sheath is being expanded or contracted with each adjustment. For example, in some aspects of the technology, the sizing device may have a scale with gradations that indicate what the outer diameter of variable size repositioning sheath will be based on the position or orientation of the inner repositioning component. In some aspects of the technology, the sizing device may have detents spaced at fixed intervals, so that the operator will get tactile feedback through handle 317 for each increment (e.g., every 0.1 Fr, every 0.5 Fr, etc.) by which the outer diameter of variable size repositioning sheath has been adjusted. In such cases, the detents may further be configured to provide some resistance or friction against the sizing device being moved, so that the sizing device will tend to hold its setting. In some aspects of the technology, the sizing device may include circuitry configured to provide audio, visual, and/or haptic feedback (or to provide signals to one or more additional components configured to produce audio, visual, and/or haptic output based thereon). In such cases, the audio, visual, and/or haptic feedback may be delivered in real-time or substantially in real-time.

In some aspects of the technology, the inner repositioning sheath component 320 may be made from a material with a low friction coefficient. For example, the inner repositioning sheath component 320 may be coated with at least one of the following low-friction materials: a hydrophilic coating; a lubricious silicone coating; a non-hydrophilic lubricious silicone coating; an MDX coating; or a PTFE coating. In addition, the inner repositioning sheath component 320 may be formed of a polymer material containing a lubricious additive (e.g., a polymer with a Mobilize additive from Compounding Solutions, LLC, or a polymer product such as a ProPell Low Friction Compound from Foster Corporation). In some aspects, vapor deposition may be used to add a low-friction coating to the inner repositioning sheath component 320, such as a fluorinated ethylene propylene (FEP), cyclic olefin copolymer (COC), or thermoplastic polyurethane (TPU). Using a low-friction material or coating for the inner repositioning sheath component 320 may help to prevent wear between the inner repositioning sheath component 320 and the outer repositioning sheath component 312, and/or between the lumen 319 of the inner repositioning sheath component 320 and the portion of the medical device passing therethrough (e.g., elongate catheter 332).

As shown in the example of FIG. 3A, and as further described below with respect to FIG. 3B, the inner repositioning sheath component may be tapered linearly. In that regard, in the example of FIG. 3A, the inner repositioning sheath component 320 is tapered uniformly at a constant angle along the length of the inner repositioning sheath, and the outer repositioning sheath component 312 has a complementary taper. In addition, as shown in the example of FIG. 4A, and as described further below with respect to FIGS. 4A-4F, the cross-section of inner repositioning sheath component may also be uniform longitudinally. In that regard, in the example of FIG. 4A, the portion of the inner repositioning sheath component 420 that acts on outer repositioning sheath component does not taper in diameter.

A handle 317 may be formed at or attached to the proximal end 326 of inner repositioning sheath component 320. For example, the handle 317 and the rest of the inner repositioning sheath component 320 may be formed from a single piece of material, or may be separate pieces that are joined together. If handle 317 is configured to attach to the distal end 326 of inner repositioning sheath component 320, then a snap fit, press fit, or any other suitable connection may be employed. In some aspects of the technology, handle 317 may be further configured to be removable from the rest of the inner repositioning sheath component 320. In the example of FIG. 3A, lumen 319 passes through handle 317. However, in some aspects of the technology, handle 317 may be configured so that it attaches to the proximal end 326 of inner repositioning sheath component 320 in a way that does not require lumen 319 to pass through it.

As already noted, in the example of FIG. 3A, the outer surface of the inner repositioning sheath component 320 and the inner surface of the outer repositioning sheath component 312 have complementary tapers. As a result of these complementary tapers, moving inner repositioning sheath component 320 in the distal direction relative to the outer repositioning sheath component 312 will cause variable size repositioning sheath 310 to expand the outer diameter of the variable size repositioning sheath 310. In addition, variable size repositioning sheath 310 may be configured such that moving inner repositioning sheath component 320 in the proximal direction relative to the outer repositioning sheath component 312 will cause or allow the variable size repositioning sheath 310 to contract the outer diameter of the variable size repositioning sheath 310. In some aspects of the technology, this relative longitudinal motion between the inner repositioning sheath component 320 and the outer repositioning sheath component 312 may be caused by an operator rotating the inner repositioning sheath component 320 (e.g., by the operator rotating the inner repositioning sheath component 320 with handle 317). For example, in some aspects of the technology, the inner repositioning sheath component 320 and outer repositioning sheath component 312 (or portions thereof) may be threaded such that rotation of the inner repositioning sheath component 320 is converted into relative longitudinal motion between the inner repositioning sheath component 320 and the outer repositioning sheath component 312. In some aspects of the technology, this relative motion between the inner repositioning sheath component 320 and the outer repositioning sheath component 312 may be caused by an operator translating the inner repositioning sheath component 320 in the proximal or distal direction (e.g., by the operator sliding the inner repositioning sheath component 320 proximally or distally with handle 317).

In some aspects of the technology, the outer surface of the inner repositioning sheath component 320 and the inner surface of the outer repositioning sheath component 312 may both be tapered in the opposite direction from what is shown in FIG. 3A, such that the outer diameter of the inner repositioning sheath component 320 and the inner diameter of the outer repositioning sheath both reduce toward their proximal ends. In such a case, moving inner repositioning sheath component 320 in the proximal direction relative to the outer repositioning sheath component 312 will cause variable size repositioning sheath 310 to expand the outer diameter of the variable size repositioning sheath 310, and moving inner repositioning sheath component 320 in the distal direction relative to the outer repositioning sheath component 312 will cause or allow variable size repositioning sheath 310 to contract the outer diameter of the variable size repositioning sheath 310.

For example, in some aspects of the technology, variable size repositioning sheath 310 may be configured such that a clockwise rotation of the inner repositioning sheath component 320 corresponds to a uniform radial contraction of the outer diameter of the outer repositioning sheath component 312, and a counterclockwise rotation of the inner repositioning sheath component 320 corresponds to a uniform expansion of the outer diameter of the outer repositioning sheath component 312. Likewise, in some aspects of the technology, variable size repositioning sheath 310 may be configured such that a counterclockwise rotation of the inner repositioning sheath component 320 corresponds to a uniform contraction of the outer diameter of the outer repositioning sheath component 312, and a clockwise rotation of the inner repositioning sheath component 320 corresponds to a uniform expansion of the outer diameter of the outer repositioning sheath component 312.

In some aspects of the technology, variable size repositioning sheath 310 may be configured such that each degree of clockwise rotation of the inner repositioning sheath component 320 corresponds to a fixed amount of radial contraction of the outer diameter of the outer repositioning sheath component 312, and each degree of counterclockwise rotation of the inner repositioning sheath component 320 corresponds to a fixed amount of expansion of the outer diameter of the outer repositioning sheath component 312. Likewise, in some aspects of the technology, variable size repositioning sheath 310 may be configured such that each degree of counterclockwise rotation of the inner repositioning sheath component 320 corresponds to a fixed amount of radial contraction of the outer diameter of the outer repositioning sheath component 312, and each degree of clockwise rotation of the inner repositioning sheath component 320 corresponds to a fixed amount of expansion of the outer diameter of the outer repositioning sheath component 312. For example, variable size repositioning sheath 310 may be configured such that a rotation of 180 degrees (e.g., half a turn of handle 317) may correspond to radial expansion or contraction of the outer diameter of the outer repositioning sheath component 312 by a fixed amount (e.g., 0.5 Fr). As another example, a rotation of 360 degrees (e.g., a full turn of handle 317) may correspond to a radial expansion or contraction of the outer diameter of the outer repositioning sheath component 312 by a fixed amount (e.g., 1 Fr).

As noted above, in some aspects of the technology, the variable size repositioning sheath 310 may be configured such that handle 317 provides feedback to the operator corresponding to a known change in the radial outer diameter of the variable size repositioning sheath 310. For example, after every fixed amount of change in the radial size (e.g., every 0.1 Fr, or every 0.5 Fr, etc.), handle 317 may provide feedback to the operator in the form of a notch in the handle "clicking," the handle vibrating or giving haptic feedback, audio feedback, or any other type of notification such that the operator can determine the current size of the variable size repositioning sheath 310.

In some aspects of the technology, variable size repositioning sheath 310 may be configured such that the operator may impart a translation motion on the inner repositioning sheath component 320 in order to cause a radial expansion or contraction of the size of the variable size repositioning sheath 310. For example, the variable size repositioning sheath 310 may be configured such that by pushing or a pulling the inner repositioning sheath component 320 (e.g., via handle 317) by a fixed amount (e.g., 1 cm), the outer diameter of the variable size repositioning sheath 310 may expand or contract by a set amount (e.g., 1 Fr). In some aspects of the technology, sizing device 300 may further include a "stepped" or "click" connector, as further described in FIG. 4F, where a fixed amount of translational motion in a proximal or distal direction corresponds to a "step" or "click," and where each "step" or "click" in the connector corresponds to a known change in the radial size of the variable size repositioning sheath 310.

Figure 3B:
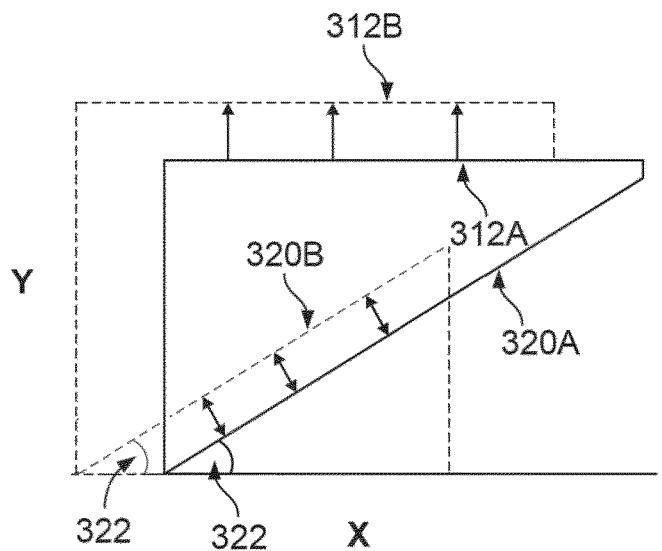
FIG. 3B is a diagram illustrating how relative movement between inner and outer components of an exemplary sizing device may create expansion or contraction, according to aspects of the disclosure.
Figure 4A:
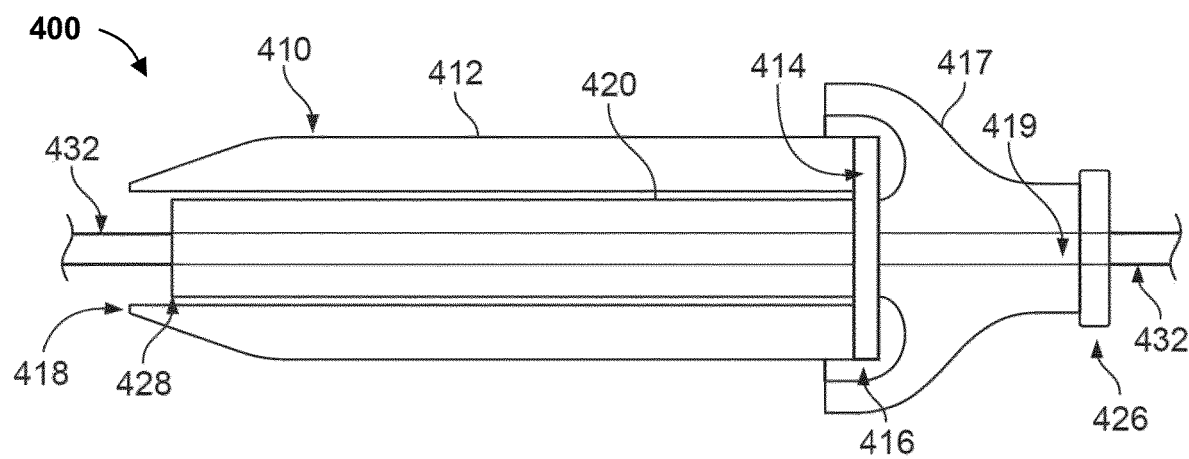
FIG. 4A shows a cross-sectional view of an example sizing device according to aspects of the disclosure.

FIG. 3B illustrates how moving the inner repositioning sheath component 320 distally relative to outer repositioning sheath component 312 (whether caused by the operator rotating or translating the inner repositioning sheath component 320) corresponds to a uniform radial expansion of the outer diameter of the outer repositioning sheath component 312. In particular, FIG. 3B illustrates how the angle 322 of the taper of inner repositioning sheath component 320 determines the change in radial size of the variable size repositioning sheath 312. In that regard, as the inner repositioning sheath component 320 moves in the x direction from position 320A to 320B, its outer surface imparts a normal force on the complementary tapered inner surface of outer repositioning sheath 312, which results in the outer surface of outer repositioning sheath 312 being pushed radially outwards from position 312A to 312B. The tangent of the taper angle 322 of the inner repositioning sheath component 320 (which is the same taper angle of outer repositioning sheath component 312) determines how much radial expansion will be caused by a given movement in the x direction. In that regard, if angle 322 is 60 degrees and an operator translates handle 317 a distance of 1 cm (or rotates handle 317 an amount necessary to translate variable size repositioning sheath 320 by 1 cm), it will result in the outer surface of the outer repositioning sheath component 312 expanding radially in all directions by [(1 cm)×tan(60°)], and the diameter of the outer repositioning sheath component 312 thus expanding by twice that amount (i.e., [2×(1 cm)×tan(60°)]). The taper angle 322 may thus be selected to obtain a desired diameter of change between an increment of handle translation and the resulting radial expansion of the repositioning sheath.

Figure 3C:
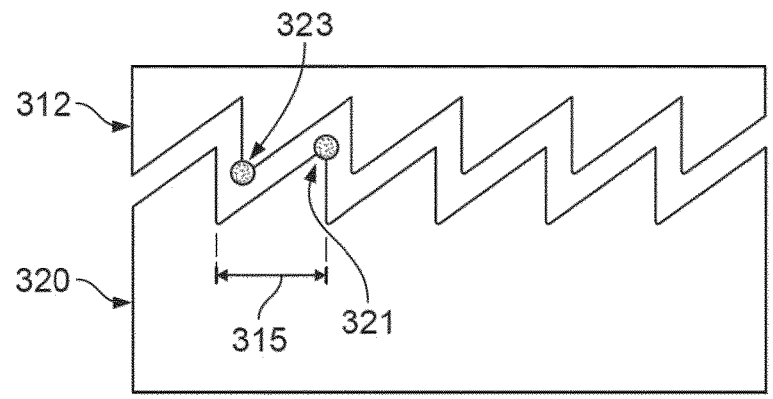
FIG. 3C shows a partial cross-sectional view of an example sizing device, according to aspects of the disclosure.

FIG. 3C is a diagram depicting a cross-sectional view of an additional example sizing device configured to expand or contract a size of a variable size repositioning sheath, according to aspects of the technology. In the example of FIG. 3C, rather than the entire outer surface of the inner repositioning sheath component 320 tapering linearly between the proximal and distal ends as shown in FIG. 3A, the outer surface (or one or more portions thereof) of the inner repositioning sheath component 320 may instead have a saw-toothed feature. Likewise, rather than the entire inner surface of the outer repositioning sheath component 312 tapering linearly between the proximal and distal ends as shown in FIG. 3A, the inner surface (or one or more portions thereof) of the outer repositioning sheath component 312 may instead have a saw-toothed feature that is complementary of the saw-toothed feature on the inner repositioning sheath 320. While for the purposes of clarity the diagram of FIG. 3C shows an accentuated gap between the complementary saw-toothed features of inner repositioning sheath component 320 and outer repositioning sheath component 312, there may be little or no gap between these surfaces when at rest, and the surfaces will come into contact when in use (as discussed below). In that regard, in the example of FIG. 3C, when the inner repositioning sheath component 320 is translated in the proximal or distal direction, the saw-toothed feature of the inner repositioning sheath component 320 will move into contact with the complementary saw-toothed feature of the outer repositioning sheath component 312, and cause it to expand or contract (or allowing it to contract) in a radial direction. For example, if an operator of the sizing device of FIG. 3C causes the inner repositioning sheath component 320 to translate by distance 315, the surfaces of each saw-tooth of the inner repositioning sheath component 320 will slide over the complementary surfaces of each saw-tooth of the outer repositioning sheath component 312 until, for example, peak 321 reaches peak 323. This relative motion will cause expansion of the outer repositioning sheath component 312 according to the same principles discussed above with respect to FIG. 3B. Likewise, if the inner repositioning sheath component 320 is then moved in the opposite direction so that peak 321 begins to move away from peak 323, the outer repositioning sheath component 312 will contract (or be allowed to contract).

In some aspects of the technology, use of a saw-toothed feature such as the one shown in FIG. 3C may help the outer repositioning sheath component 312 expand and contract more uniformly over its entire length, and thus may reduce bending and deformation. In some aspects of the technology, the operator may impart translational motion on the inner repositioning sheath component 320 by pushing or pulling the inner repositioning sheath component 320 or a handle attached thereto, as discussed above. In some aspects of the technology, the operator may impart translational motion on the inner repositioning sheath component 320 by rotating the inner repositioning sheath component 320 or a handle attached thereto, as discussed above. In such cases, while the saw-toothed features of the inner repositioning sheath component 320 and the outer repositioning sheath component 312 are not threads, there may be a threaded connection on some other portion of the interface between the inner repositioning sheath component 320 and the outer repositioning sheath component 312 such that rotating the inner repositioning sheath component 320 may cause it to move translationally relative to the outer repositioning sheath component 312.

FIG. 4A depicts an example sizing device configured to expand or contract a size of a variable size repositioning sheath, according to aspects of the technology. In that regard, sizing device 400 comprises variable size repositioning sheath 410 that includes an outer repositioning sheath component 412 with hub 414, inner repositioning sheath component 420, and handle 417. The outer repositioning sheath component 412 includes a distal end 418, a proximal end 416, and a cylindrical or substantially cylindrical cavity or lumen extending therethrough between the proximal and distal ends. The inner repositioning sheath component 420 is disposed within the cavity or lumen of outer repositioning sheath component 412. The portion of inner repositioning sheath 320 that is disposed within the cavity or lumen of outer repositioning sheath component 412 is also cylindrical or substantially cylindrical, and may be configured as further described below with respect to the example cross-sections of FIG. 4A illustrated in FIGS. 4B-4F. Inner repositioning sheath 420 comprises a distal end 428, a proximal end 426, and a lumen 419 extending therethrough between the proximal and distal ends, such that elongate catheter 432 may be inserted through lumen 419. A handle 417 is arranged at the proximal end 426 of inner repositioning sheath component 420. In some aspects of the technology, handle 417 may be replaced with a level, tab, gear, or any other device suitable for moving inner repositioning sheath component 420. Other than as described below, sizing device 400 may have the same functionality and components as sizing device 300, as described above in reference to FIGS. 3A-3C.

In some aspects of the technology, the inner repositioning sheath component 420 may be more rigid than the outer repositioning sheath component 412. In some aspects of the technology, the inner repositioning sheath component 420 may be reinforced with a sleeve of a different material. For example, the inner repositioning sheath component 320 may be a polymer and it may be reinforced with a metal sleeve. In some aspects of the technology, the inner repositioning sheath component 420 may be made of a material with a greater strength than the outer repositioning sheath component 412. In some aspects of the technology, the inner repositioning sheath component 420 may comprise a metal frame. Allowing inner repositioning sheath component 420 to be more rigid than the outer variable size repositioning sheath component 412 may help to prevent or limit deformation of the inner repositioning sheath component 420 when it acts on the outer repositioning sheath component 412 to expand or contract the outer diameter of the variable size repositioning sheath 410.

In some aspects of the technology, the inner repositioning sheath component 420 may be configured as a hollow mandrel such that elongate catheter 432 may be inserted through the lumen of the mandrel. In some aspects of the technology, the inner repositioning sheath component 420 may have different cross-sectional areas that determine the expansion or contraction of the size of the variable size repositioning sheath body 412, as described in detail in reference to FIGS. 4B-4E.

In some aspects of the technology, variable size repositioning sheath 410 may be configured such that moving inner repositioning sheath component 420 may cause it to act on the outer repositioning sheath component 412, thus radially expanding or contracting the size of the variable size repositioning sheath 410. For example, a rotational motion of the inner repositioning sheath component 420 (e.g., an operator rotating the inner repositioning sheath component 420 with handle 417) may correspond to a radial expansion or a contraction of the outer diameter of the outer repositioning sheath component 412. In that regard, in some aspects of the technology, variable size repositioning sheath 410 may be configured such that a clockwise rotation of the inner repositioning sheath component 420 corresponds to a uniform radial contraction of the outer diameter of the outer repositioning sheath component 412, and a counterclockwise rotation of the inner repositioning sheath component 420 corresponds to a uniform expansion of the outer diameter of the outer repositioning sheath component 412. Likewise, in some aspects of the technology, variable size repositioning sheath 410 may be configured such that a counterclockwise rotation of the inner repositioning sheath component 420 corresponds to a uniform radial contraction of the outer diameter of the outer repositioning sheath component 412, and a clockwise rotation of the inner repositioning sheath component 420 corresponds to a uniform radial expansion of the outer diameter of the outer repositioning sheath component 412.

In some aspects of the technology, variable size repositioning sheath 410 may be configured such that a degree of rotation of the inner repositioning sheath component 420 corresponds to a set amount of expansion or contraction of the outer diameter of the outer repositioning sheath component 412. For example, variable size repositioning sheath 410 may be configured such that a rotation of 180 degrees (e.g., half a turn of handle 317) may correspond to radial expansion or contraction of the outer diameter of the outer repositioning sheath component 412 by a fixed amount (e.g., 0.5 Fr). As another example, a rotation of 360 degrees (e.g., a full turn of handle 317) may correspond to a radial expansion or contraction of the outer diameter of the outer repositioning sheath component 412 by a fixed amount (e.g., 1 Fr).

Figure 4B:
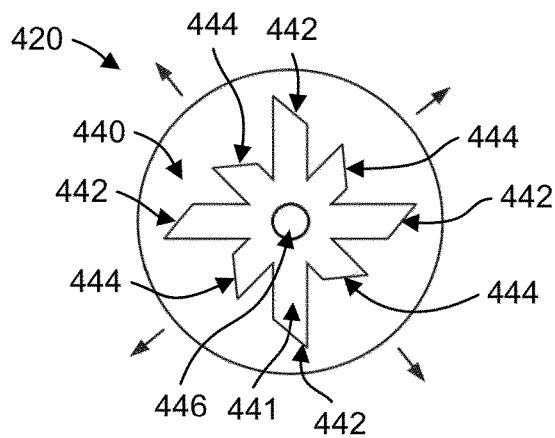
FIG. 4B shows a cross-sectional view of an example inner repositioning sheath component, according to some aspects of the disclosure.

FIG. 4B shows a cross-sectional area of an example inner repositioning sheath component 420, according to some aspects of the technology. In the example of FIG. 4B, inner repositioning sheath component 420 has a ratchet-type or gear-type mechanism comprised of an outer ratchet component 440 and an inner ratchet component 441. Inner ratchet component 441 has an alternating series of long teeth 442 and short teeth 444, and outer ratchet component 440 has a corresponding pattern of long and short voids into which each of these teeth may fit. Inner ratchet component 441 may be rotated relative to outer ratchet component 440, causing each long tooth 442 to shift into a short void of outer ratchet component 440 (and causing each short tooth 444 to shift into a long void of outer ratchet component 440), thus causing outer ratchet component 440 to be expanded in the radial direction. The expansion of outer ratchet component 440 in turn acts on outer repositioning sheath component 412 to expand the size of the variable size repositioning sheath 410, as discussed above. With an additional rotation in the same direction, each long tooth 442 will be shifted back into a long void of outer ratchet component 440, and each short tooth 444 will shift back into a short void of outer ratchet component 440, thus allowing outer ratchet component 440 to contract again in the radial direction (and thus allowing the variable size repositioning sheath 410 to contract, as discussed above). In some aspects of the technology, inner ratchet component 441 may be comprised of a stronger material than outer ratchet component 440. In some aspects of the technology, outer ratchet component 440 may be comprised of a flexible material such as one of the polymers mentioned above. In some aspects of the technology, inner ratchet component 441 may be comprised of a rigid material such as a metal. Inner ratchet component 441 has a hole 446 which may form a part of lumen 419.

Although the example of FIG. 4B shows four long teeth 442 and four short teeth 444, any suitable number of teeth may be used. Similarly, although the teeth 442 and 444 of FIG. 4B have straight edges, any suitable shape and profile of teeth may be used. In some aspects of the technology, the size of the long teeth 442 and short teeth 444 (and thus the corresponding size of the long and short voids in outer ratchet component 440) may be selected to provide a specific amount of expansion and contraction. For example, the size of the long teeth 442 and short teeth 444 (and the corresponding size of the long and short voids in outer ratchet component 440) may be configured such that variable size repositioning sheath 410 will fit into the arteriotomy left by a standard size peel-away introducer sheath (e.g., a 17.9 Fr arteriotomy) when in its expanded state, and will fit into a smaller expandable introducer sheath (e.g., with a 14 Fr inner diameter) when in its contracted state.

Figure 4C:
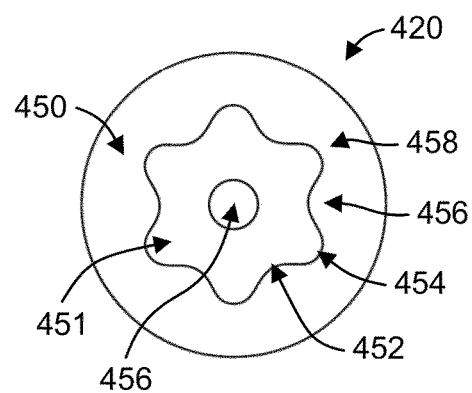
FIG. 4C shows a cross-sectional view of an example inner repositioning sheath component, according to some aspects of the disclosure.

FIG. 4C shows a cross-sectional area of an example inner repositioning sheath component 420, according to some aspects of the technology. In the example of FIG. 4C, inner repositioning sheath component 420 has a cam-type mechanism comprised of an outer cam component 450 and an inner cam component 451. Inner cam component 451 has an alternating series of valleys 452 and peaks 444, and outer cam component 450 has a void with a corresponding profile consisting of thicker sections 456 and thinner sections 458 into which the valleys 452 and peaks 454 may fit. Inner cam component 451 may be rotated relative to outer cam component 450, causing each peak 454 to press against a thicker section 456 of outer cam component 450, and causing each valley 452 to shift into a thinner section 458 of outer cam component 450, thus causing outer cam component 450 to be expanded in the radial direction. The expansion of outer cam component 450 in turn acts on outer repositioning sheath component 412 to expand the size of the variable size repositioning sheath 410, as discussed above. With an additional rotation in either direction, each peak 454 will be shifted back into a thinner section 458 of outer cam component 450, and each valley 452 will shift back into a thicker section 456 of outer cam component 450, thus allowing outer cam component 450 to contract again in the radial direction (and thus allowing the variable size repositioning sheath 410 to contract, as discussed above). In some aspects of the technology, inner cam component 451 may be comprised of a stronger material than outer cam component 450. In some aspects of the technology, outer cam component 450 may be comprised of a flexible material such as one of the polymers mentioned above. In some aspects of the technology, inner cam component 451 may be comprised of a rigid material such as a metal. Inner cam component 451 has a hole 456 which may form a part of lumen 419.

Although the example of FIG. 4C shows six valleys 452 and six peaks 454, any suitable number of peaks and valleys may be used. Similarly, any suitable shape and profile of peaks and valleys may be used such as round, eccentric, oval, elliptical, hexagonal, star-shaped, etc. In some aspects of the technology, the size of the valleys 452 and peaks 454 (and thus the corresponding size of the thicker sections 456 and thinner sections 458 in outer cam component 450) may be selected to provide a specific amount of expansion and contraction. For example, the size of the valleys 452 and peaks 444 (and corresponding size of the thicker sections 456 and thinner sections 458) may be configured such that variable size repositioning sheath 410 will fit into the arteriotomy left by a standard size peel-away introducer sheath (e.g., a 17.9 Fr arteriotomy) when in its expanded state, and will fit into a smaller expandable introducer sheath (e.g., with a 14 Fr inner diameter) when in its contracted state.

Figure 4D:
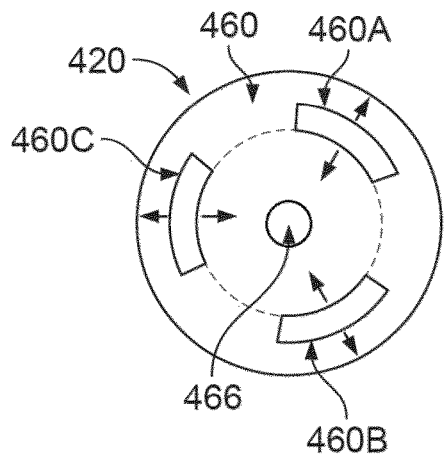
FIG. 4D shows a cross-sectional view of an example inner repositioning sheath component, according to some aspects of the disclosure.

FIG. 4D shows a cross-sectional area of an example inner repositioning sheath component 420, according to some aspects of the technology. In the example of FIG. 4D, inner repositioning sheath component 420 has a mandrel-type mechanism. In that regard, FIG. 4D shows a mandrel-type inner repositioning sheath component 460, which comprises a hole 466 (which may form a part of lumen 419) and mandrel components 460A-460C. Mandrel-type inner repositioning sheath component 460 would be mounted on a hub (not shown) configured to actuate mandrel components 460A-460C, such as a hub with a stepped connector like the one described below with respect to FIG. 4F. In that regard, when the mandrel-type inner repositioning sheath component 460 is rotated relative to its hub, the hub imparts force on mandrel components 460A, 460B, and 460C such that they expand radially outwards, which in turn expands inner repositioning sheath component 420 and variable size repositioning sheath 410 as discussed above. Similarly, in some aspects of the technology, when the mandrel-type inner repositioning sheath component 460 is rotated relative to its hub, the hub imparts force on (or ceases to impart force on) mandrel components 460A, 460B, and 460C such that they contract radially outwards, which in turn causes or allows the inner repositioning sheath component 420 and variable size repositioning sheath 410 to contract as discussed above. In some aspects of the technology, the mandrel-type inner repositioning sheath component 460 may be configured to contract radially inwards in response to a clockwise rotation and expand radially outwards in response to a counterclockwise rotation. In some aspects of the technology, the mandrel-type inner repositioning sheath component 460 may be configured to contract radially inwards in response to a counterclockwise rotation and expand radially outwards in response to a clockwise rotation.

Figure 4E:
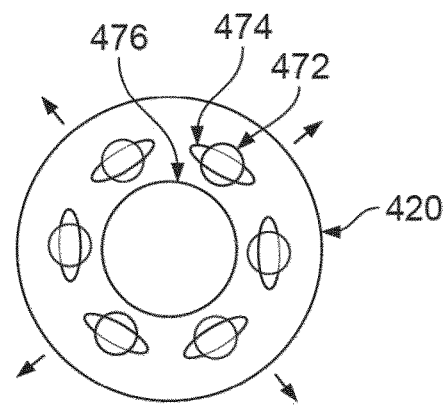
FIG. 4E shows a cross-sectional view of an example inner repositioning sheath component, according to some aspects of the disclosure.
Figure 4F:
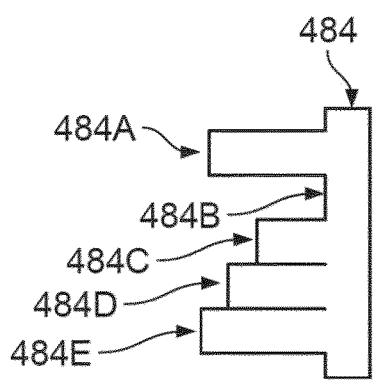
FIG. 4F illustrates a cross-section of an example stepped structure configured to be disposed in a variable size repositioning sheath hub, according to aspects of the disclosure.

In some aspects of the technology, the mandrel-type inner repositioning sheath component 460 and its hub may be configured with a set number of sizes that the mandrel components 460A-460C can radially expand or contract into, as further described in reference to FIG. 4F. For example, the mandrel-type inner repositioning sheath component 460 and its hub may be configured with five different sizes. For example, one of the five sizes may be preset to adjust the diameter of the variable size repositioning sheath 410 to a size that would fit into the arteriotomy left by a standard size peel-away introducer sheath (e.g., a 17.9 Fr arteriotomy); a second of the five sizes may be preset to produce a diameter of the variable size repositioning sheath 410 that will fit into a smaller expandable introducer sheath (e.g., with a 14 Fr inner diameter); and the other three sizes may be preset to produce diameters between the first and second sizes, to accommodate patient-specific and procedure-specific criteria.

FIG. 4E shows a cross-sectional area of an example inner repositioning sheath component 420, according to some aspects of the technology. In the example of FIG. 4E, inner repositioning sheath component 420 has set of channels 472 through which a set of oval-shaped interstitial rods 474 pass. The interstitial rods 474 are connected to a hub (not shown) configured to rotate each rod 474 within its respective channel 472. In the example of FIG. 4E, inner repositioning sheath component 420 comprises a material that is sufficiently elastic to allow channels 472 to deform as the interstitial rods 474 are rotated. In that regard, when oval-shaped interstitial rods 474 are rotated 90 degrees from the tangential orientation shown in FIG. 4E (i.e., in which the long axis of each oval is tangential to the center point of inner repositioning sheath component 420) to a radial orientation, the channels 472 will deform in the radial direction, thus expanding the outer diameter of the inner repositioning sheath component 420 (and thus the variable size repositioning sheath 410, as discussed above). Likewise, when oval-shaped interstitial rods 474 are rotated another 90 degrees from the radial orientation back to the tangential orientation shown in FIG. 4E, the channels 472 will relax in the radial direction and deform in the tangential direction, thus contracting the outer diameter of the inner repositioning sheath component 420 (and thus the variable size repositioning sheath 410, as discussed above). In some aspects of the technology, inner repositioning sheath component 420 may further include a rigid inner sleeve (not shown) configured to prevent the deformation resulting from the rotation of interstitial rods 474 from increasing or decreasing the size of hole 476. As above, hole 476 may form a part of lumen 419. Although the example of FIG. 4E depicts oval-shaped interstitial rods 474 and circular channels 472, the interstitial rods and channels may be any shape suitable for creating deformation when interstitial rods 472 are rotated within channels 474.

FIG. 4F illustrates a cross-section of an example stepped structure configured to be disposed in a variable size repositioning sheath hub, according to some aspects of the technology. The stepped structure 484 is configured to be disposed in a variable size repositioning sheath hub, which may further be lockingly connected into an introducer sheath hub (e.g., introducer sheath hub 124), as described above. In some aspects of the technology, the stepped structure 484 may be an integral part of the variable size repositioning sheath hub. In the example of FIG. 4F, the stepped structure 484 has a set of locking steps 484A-484E of different lengths. A variable size repositioning sheath hub with a stepped structure 484 may be configured such that, when it is rotated relative to a component of the inner repositioning sheath component 412 (e.g., the mandrel-type inner repositioning sheath component 460), a single locking step of the locking steps 484A-484E will engage a component of the inner repositioning sheath component 412 at a time. For example, when a variable size repositioning sheath hub with a stepped structure 484 is used in conjunction with the example sizing device of FIG. 4D, the variable size repositioning sheath hub may be configured such that rotating one relative to the other (e.g., by rotating handle 417) will cause locking steps 484A-484E to successively engage the mandrel components 460A-460C, and thus cause the outer diameter of inner repositioning sheath component 420 to change by fixed amounts determined by the size of each locking step. In some aspects of the technology, the locking steps 484A-484E may be selected to change the diameter of the variable size repositioning sheath 410 by a fixed amount of French, or to produce sizes that correspond to expected uses (e.g., for use with a standard size peel-away introducer sheath (e.g., a 17.9 Fr arteriotomy), a smaller expandable introducer sheath (e.g., with a 14 Fr inner diameter), etc.). While the example of FIG. 4F includes five locking steps 484A-484E, any number of steps may be used. For example, a higher number of locking steps (e.g., anywhere from 10-100) may be used for more refinement and precision when changing the size of the variable size repositioning sheath (e.g., changing the size in steps sizes of 0.5 Fr with 5 steps vs. changing the size in step sizes of 0.05 Fr with 50 steps).

FIG. 5 shows an example placement system comprising a variable size repositioning sheath inserted into the arteriotomy after an intracardiac device 518 has been inserted through an introducer sheath and into a patient's vasculature, according to some aspects of the disclosure. The placement system 500 includes handle 502, sterile sleeve 504, Tuohy Borst adapter 508, hemostasis stylet 510, elongate catheter 506, variable size repositioning sheath 514 with hub 512 attached at the proximal end of the variable size repositioning sheath 514, insertion site 516, and intracardiac device 518. The handle 502 is proximal to the sterile sleeve 504. The sterile sleeve 504 is distal to handle 502 and proximal to Tuohy-Borst adaptor 508. The hemostasis stylet 510 is connected at its proximal end to the distal end of the Tuohy-Borst adaptor 508. Elongate catheter 506 is inserted through an inner lumen of the sterile sleeve 504, an inner lumen of the Tuohy-Borst 508 adaptor, an inner lumen of hemostasis stylet 510, and an inner lumen of variable size repositioning sheath 514.

In some aspects of the technology, elongate catheter 506 may be a 9 Fr catheter. In some aspects of the technology, hub 512 of variable size repositioning sheath 514 may be configured to clamp or tighten down on elongate catheter 506 to stabilize the elongate catheter 506 and prevent it from moving longitudinally relative to variable size repositioning sheath 514.

In some aspects of the technology, gap 507 between hemostasis stylet 510 and hub 512 may create a sterile barrier for elongate catheter 506. For example, hub 512 may be clamped or tightened around elongate catheter 506 to ensure that a gap 507 is maintained between the distal end of the hemostasis stylet 510 and hub 512.

FIG. 6 shows an example placement system comprising a variable size repositioning sheath inserted into the arteriotomy after an intracardiac device 618 has been inserted through an introducer sheath and into a patient's vasculature, according to some aspects of the disclosure. The placement system 600 includes handle 602, sterile sleeve 604, Tuohy Borst adapter 608, hemostasis stylet 610, elongate catheter 606, hub 612, variable size repositioning sheath 614, insertion site 616, and intracardiac device 618. The handle 602 is proximal to the sterile sleeve 604. The sterile sleeve 604 is distal to handle 602 and proximal to Tuohy Borst adaptor 608. The hemostasis stylet 610 is connected at its proximal end to the distal end of the Tuohy Borst adaptor 608. The hemostasis stylet 610 is inserted into an inner lumen of variable size repositioning sheath 614 at the proximal end of variable size repositioning sheath 614. Elongate catheter 606 is inserted through an inner lumen of the sterile sleeve 604, an inner lumen of the Tuohy Borst 608 adaptor, an inner lumen of hemostasis stylet 610, and an inner lumen of variable size repositioning sheath 614. There is no gap between hemostasis stylet 610 and variable size repositioning sheath 614 because the hemostasis stylet 610 is inserted into the variable size repositioning sheath 614.

In some aspects of the technology, elongate catheter 606 may be a 9 Fr catheter. n some aspects of the technology, hub 612 of variable size repositioning sheath 614 may be configured to clamp or tighten down on elongate catheter 606 to stabilize the elongate catheter 606 and prevent it from moving longitudinally relative to variable size repositioning sheath 614.

In the example of FIG. 6, the portion of the elongate catheter 606 proximal to hub 612 is covered by sterile sleeve 604. In some aspects of the technology, the sterile sleeve 604 may be comprised of polyolefin, polyethylene, low-density polyethylene (LDPE), linear low-density polyethylene (LLDPE), medium-density polyethylene (MDPE), or high-density polyethylene (HDPE).

In some aspects of the technology, the hemostasis stylet 610 may be configured to lock to hub 612 of the variable size repositioning sheath 614. In that regard, the hemostasis stylet 610 may be configured to lock to hub 612 using any suitable locking mechanism, such as a twist lock, a pop lock, a locking pin, or any other comparable locking mechanism. In some aspects of the technology, in addition to the hemostasis stylet 610 being configured to lock to hub 612, the hub 612 may also be configured to fix the elongate catheter 606 in place (e.g., using a clamp or fastening means). Locking the hemostasis stylet 610 to hub 612 and locking hub 612 around elongate catheter 606 may control hemostasis between the variable size repositioning sheath 614 and an opening of a blood vessel, and may further help to control blood flow along the variable size repositioning sheath and reduce potential ischemia.

In addition to the advantages discussed above, the variable size repositioning sheath assemblies herein may also be advantageous over existing expandable sheath assemblies because they maintain guidewire access throughout the full procedure by always allowing the operator to remove the pump with the repositioning sheath in place.

The foregoing description is merely intended to be illustrative of the principles of the technology. As such, the devices and methods described herein can be practiced by other than the described implementations, which are presented for purposes of illustration and not of limitation. It is to be understood that the systems, devices and methods disclosed herein, while described with respect to use in percutaneous insertion of blood pumps, may be applied in any context where a device is to be inserted into a patient and hemostasis is required. In addition, the disclosed features may be implemented in any combination or subcombination (including multiple dependent combinations and subcombinations) with one or more other features described herein. The various features described or illustrated above, including any components thereof, may also be combined or integrated into other systems. Finally, certain features may be omitted or not implemented without departing from the spirit of the technology.

The invention claimed is:

1. A variable size repositioning sheath comprising:
   a sheath body having a length, the sheath body including:
      an outer repositioning sheath component, and
      an inner repositioning sheath component disposed at least partially within the outer repositioning sheath component wherein the inner repositioning sheath comprises at least one mandrel component; and
   a stepped structure comprising a plurality of variable length steps configured to cooperate with the inner repositioning sheath component to advance the at least one mandrel components radially to cause the variable size repositioning sheath to change in size in a radial direction along at least a portion of the length of the sheath body, wherein each of the plurality of variable length steps advances the at least one mandrel component radially by a fixed amount that corresponds to a length of the variable length step engaging the at least one mandrel component,
   wherein the variable size repositioning sheath is configured to change in size in the radial direction along at least the portion of the length of the sheath body based on the at least on mandrel component of the inner repositioning sheath component moving translationally or rotationally relative to the outer repositioning sheath component.

2. The variable size repositioning sheath of claim 1, wherein the stepped structure is configured to cause an outer diameter of the inner repositioning sheath component to change by fixed amounts.

3. The variable size repositioning sheath of claim 1, wherein the stepped structure includes a plurality of locking steps, the plurality of locking steps corresponding to the fixed amounts.

4. A sheath assembly for insertion of a medical device into a blood vessel, the sheath assembly comprising:
   an introducer sheath; and
   a variable size repositioning sheath comprising:
      a sheath body having a length, the sheath body including:
         an outer repositioning sheath component, and
         an inner repositioning sheath component disposed at least partially within the outer repositioning sheath component; and
      a stepped structure configured to cause the variable size repositioning sheath to change in size in a radial direction along at least a portion of the length of the sheath body by fixed amounts,
      wherein the variable size repositioning sheath is configured to change in size in the radial direction along at least the portion of the length of the sheath body based on the inner repositioning sheath component moving translationally or rotationally relative to the outer repositioning sheath component.

5. The sheath assembly of claim 4, wherein the introducer sheath is an expandable introducer sheath.

6. The sheath assembly of claim 4, wherein the introducer sheath is a peel-away introducer sheath having a body with a fixed outer diameter.

7. The sheath assembly of claim 6, wherein the variable size repositioning is configured to change in size between at least a first state and a second state along at least the portion of the length of the sheath body of the sheath body.

8. The sheath assembly of claim 7, wherein, when the variable size repositioning sheath is in the first state, an outer diameter of the variable size repositioning sheath is larger than the fixed outer diameter, and
   wherein when the variable size repositioning sheath is in the second state, the outer diameter of the variable size repositioning sheath is smaller than the fixed outer diameter.

9. The sheath assembly of claim 4, wherein the inner repositioning sheath component is a mandrel-type component.

10. The sheath assembly of claim 4, wherein the stepped structure is configured to cause an outer diameter of inner repositioning sheath component to change by the fixed amounts.

11. A blood pump system, comprising:
    an intracardiac device comprising a pump and a cannula, the pump having a pump housing, a rotor, and an opening in the pump housing, the cannula having a proximal end that interfaces with a distal end of the pump housing and a distal end with at least one distal opening, the pump being configured to be operated by a motor;
    an elongate catheter coupled on its distal end to the motor or to the pump housing; and
    a sheath assembly, comprising:
       an introducer sheath configured to introduce the intracardiac device into a blood vessel; and
       a variable size repositioning sheath comprising:
          a sheath body having a length, the sheath body including:
             an outer repositioning sheath component, and
             an inner repositioning sheath component disposed at least partially within the outer repositioning sheath component; and,
          a stepped structure configured to cause the variable size repositioning sheath to change in size in a radial direction along at least a portion of the length of the sheath body by fixed amounts,
          wherein the variable size repositioning sheath is configured to change in size in the radial direction along at least the portion of the length of the sheath body based on the inner repositioning sheath component moving translationally or rotationally relative to the outer repositioning sheath component.

12. The blood pump system of claim 11, wherein the inner repositioning sheath component is a mandrel-type component.

13. The blood pump system of claim 11, wherein the stepped structure is configured to cause an outer diameter of inner repositioning sheath component to change by the fixed amounts.

* * * * *

UNITED STATES PATENT AND TRADEMARK OFFICE
CERTIFICATE OF CORRECTION

PATENT NO.        : 12,369,944 B2
APPLICATION NO.   : 18/418468
DATED             : July 29, 2025
INVENTOR(S)       : Glen Fantuzzi et al.

Page 1 of 1

It is certified that error appears in the above-identified patent and that said Letters Patent is hereby corrected as shown below:

In the Claims

Claim 1:
Column 33, Line 23:
Now reads: "at least on mandrel"; should read -- at least one mandrel --

Signed and Sealed this
Thirtieth Day of September, 2025

John A. Squires
*Director of the United States Patent and Trademark Office*